US011571328B2

(12) United States Patent
Deckman et al.

(10) Patent No.: US 11,571,328 B2
(45) Date of Patent: Feb. 7, 2023

(54) IUD INSERTION DEVICES

(71) Applicant: MEDICINES360, San Francisco, CA (US)

(72) Inventors: Rob Deckman, San Bruno, CA (US); Mark Robert Sponsel, Sunnyvale, CA (US); Dan Hovde, Coon Rapids, MN (US); Curt Guyer, Dublin, CA (US)

(73) Assignee: MEDICINES360, San Francisco, CA (US)

( * ) Notice: Subject to any disclaimer, the term of this patent is extended or adjusted under 35 U.S.C. 154(b) by 521 days.

(21) Appl. No.: 16/376,436

(22) Filed: Apr. 5, 2019

(65) Prior Publication Data

US 2019/0307600 A1 Oct. 10, 2019

Related U.S. Application Data

(60) Provisional application No. 62/729,793, filed on Sep. 11, 2018, provisional application No. 62/654,688, filed on Apr. 9, 2018.

(51) Int. Cl.
*A61F 6/18* (2006.01)
*A61F 6/14* (2006.01)

(52) U.S. Cl.
CPC ................ *A61F 6/18* (2013.01); *A61F 6/144* (2013.01)

(58) Field of Classification Search
CPC ... A61F 6/18; A61F 6/144; A61F 6/12; B26B 1/08
USPC .......................................................... 128/833
See application file for complete search history.

(56) References Cited

U.S. PATENT DOCUMENTS

| | | | |
|---|---|---|---|
| 3,407,806 | A | 10/1968 | Hulka et al. |
| 3,783,861 | A | 1/1974 | Abramson |
| 3,794,025 | A | 2/1974 | Lerner |
| 3,902,483 | A | 9/1975 | Place et al. |
| 3,937,217 | A | 2/1976 | Kosonen |
| 4,353,363 | A | 10/1982 | Quesada |
| 4,359,046 | A | 11/1982 | Shaw, Jr. |
| 4,372,302 | A | 2/1983 | Akerlund |
| 4,381,001 | A | 4/1983 | Shaw, Jr. |
| 4,495,934 | A | 1/1985 | Shaw, Jr. |
| 4,830,025 | A | 5/1989 | Gainutdinova et al. |
| 4,920,727 | A | 5/1990 | Ristimaki et al. |
| 4,949,732 | A | 8/1990 | Spoon et al. |
| 4,957,119 | A | 9/1990 | Nijs |
| 5,084,004 | A | 1/1992 | Ranoux |
| 5,088,505 | A | 2/1992 | Nijs |
| 5,368,045 | A | 11/1994 | Clement et al. |
| 5,370,129 | A | 12/1994 | Diaz et al. |
| 5,400,804 | A | 3/1995 | Helle et al. |
| 5,785,053 | A | 7/1998 | Macandrew et al. |

(Continued)

FOREIGN PATENT DOCUMENTS

| | | | |
|---|---|---|---|
| AU | 2015221468 | A1 | 9/2015 |
| KR | 1020130012499 | A | 2/2013 |

(Continued)

*Primary Examiner* — Ophelia A Hawthorne
*Assistant Examiner* — Kevin S Albers
(74) *Attorney, Agent, or Firm* — Buchalter Cecily Anne O'Regan

(57) ABSTRACT

Single-handed IUD insertion devices, methods and kits are disclosed. The single-handed IUD insertion devices have a plurality of flexing detent arms to control axial movement of the 641 elongated guide and string control slider during use.

35 Claims, 35 Drawing Sheets

(56) References Cited

U.S. PATENT DOCUMENTS

| | | | | |
|---|---|---|---|---|
| 6,039,968 | A | | 3/2000 | Nabahi |
| 6,056,976 | A | | 5/2000 | Markkula et al. |
| 6,063,395 | A | | 5/2000 | Markkula et al. |
| 6,101,721 | A | * | 8/2000 | Medhurst .................. B26B 1/08 30/162 |
| 6,103,256 | A | | 8/2000 | Nabahi |
| 6,117,442 | A | | 9/2000 | Markkula et al. |
| 7,862,552 | B2 | | 1/2011 | McIntyre et al. |
| 10,028,858 | B2 | | 7/2018 | Deckman et al. |
| 2005/0045183 | A1 | | 3/2005 | Callister et al. |
| 2008/0095825 | A1 | | 4/2008 | Lafont |
| 2011/0083326 | A1 | * | 4/2011 | Sullivan .................... B26B 1/10 30/162 |
| 2011/0319908 | A1 | | 12/2011 | Thenuwara et al. |
| 2013/0014762 | A1 | * | 1/2013 | Deckman ................ A61F 6/144 128/833 |
| 2017/0021511 | A1 | * | 1/2017 | Chiu ....................... B26B 5/003 |
| 2018/0055684 | A1 | * | 3/2018 | Lad ......................... A61F 6/144 |

FOREIGN PATENT DOCUMENTS

| | | | |
|---|---|---|---|
| WO | 2009060077 | A2 | 5/2009 |
| WO | 2010031899 | A1 | 3/2010 |
| WO | 2019199669 | A1 | 10/2019 |

* cited by examiner

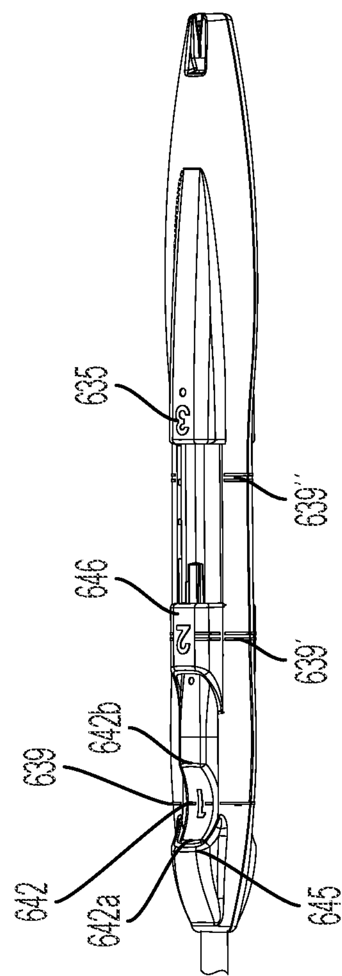
FIG. 17A
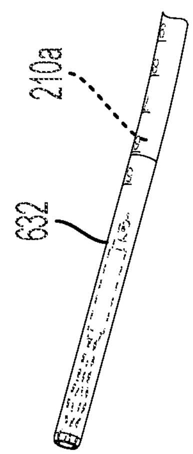

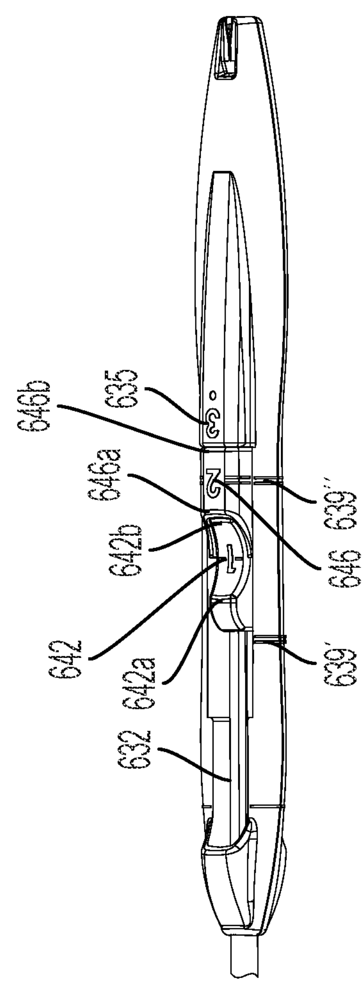
FIG. 17C
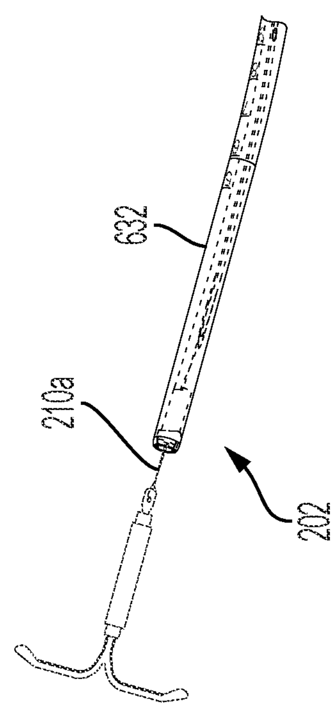

IUD INSERTION DEVICES

CROSS-REFERENCE

This application claims the benefit of U.S. Provisional Application Nos. 62/654,688, filed Apr. 9, 2018, entitled IUD INSERTION DEVICES, AND RELATED METHODS AND KITS THEREFOR, and 62/729,793, filed Sep. 11, 2018, entitled IUD INSERTION DEVICES, AND RELATED METHODS AND KITS THEREFOR which applications are incorporated herein in their entirety by reference.

BACKGROUND

Field of the Invention

The disclosure relates to intrauterine systems (IUS), intrauterine devices (IUDs), insertion devices, methods of use, and kits therefor.

Background of the Invention

An intrauterine device (IUD) is an object that, when placed in the uterus of a female, acts as a birth control device to prevent pregnancy. Two types of IUDs are commonly available, copper-containing devices and hormone-containing devices that release a progestogen. Hormonal containing devices are considered to be a different form of birth control and may be distinguished in the literature by the term intrauterine system (IUS).

Copper IUDs work by negatively affecting the mobility of sperm and preventing the sperm from joining an egg. Additionally, the foreign copper body positioned within the uterus also irritates the lining of the uterus and uterine wall making it difficult for an embryo to plant in the wall if the egg is fertilized by the sperm. IUS devices, such as the hormonal IUD Mirena® (marketed by Bayer) reduce or prevent menstrual bleeding. The Mirena® device releases levonorgestresl (a progestogen).

Conventional insertion devices used with IUDs (which includes devices used for IUSs) can cause pain and even loss of consciousness to a patient during the insertion procedure as a result of induction of a vagal reflex response.

As will be appreciated by those skilled in the art, a variety of shapes and sizes have been previously disclosed for IUD devices. Additionally, IUDs are typically inserted using an insertion device or instrument.

Thus, there exists a need for insertion devices adaptable and configurable for use with IUDs and related methods and kits which are easy-to-use, and operate smoothly for a healthcare practitioner using a single hand.

SUMMARY

Disclosed is an insertion device for use with an IUD. The insertion device has a handle and an elongated sheath. Two curved members forming cavities for a pair of sliders are positioned at a proximal end of the handle and a distal end of the handle. A sheath slider is positioned distally and is configurable to slide proximally within a portion of the distal cavity. When the sheath slider moves proximally, the sheath slider engages a string control slider. The sheath slider and the string control slider are configurable to engage and operate integrally when further proximal movement occurs. A small amount of force, e.g., from 0.25 to 0.75 lbs, more preferably from 0.5 to 0.75 lbs moves the sheath slider from an initial position to a second position. The small amount of force helps avoid or minimize incomplete insertions of an IUD by providing additional stability while the user loads the IUD and inserts the insertion device holding the IUD into a patient. The sheath slider is configurable so that it does not move past the string control slider. This ensures that the string control slider is moved all the way to the proximal position allowing the release of the strings of the IUD. The configuration of the insertion device eliminates the need for an inner sleeve at a distal position within the sheath. A hard stop feature is positioned within an interior of the handle assembly. Three pairs of detent features are positioned within the interior of the housing along the length of the housing. All three detent features have a plane of action oriented 90 degrees from a plane of ultrasonic welding of the handles. Positioning the detent features 90 degrees from the plane of the ultrasonic weld minimizes any influence of the ultrasonic welding process on a detent force value. The main slider will have additional tensile holding features to secure the tube and minimize the change of the tube dislodging from the main slider. Additional torsional holding features are also provided to secure the main tube to the handle to minimize the chance of the tube rotating within the main slider. Additional strengtheners are positioned inside the handle around the weld area to minimize the handle haves from separating during removal from the packaging. The sharp edge of the cleft has been rounded to minimize breakage of the IUD strings and the string control slider and string guide are molded into a single part.

An aspect of the disclosure is directed to insertion devices for inserting an IUD. Insertion devices comprise: an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, a rail along a side of the moveable sheath slider and a lateral detent arm, and a string control slider having a curved distal surface for abutting with the curved surface of the moveable sheath slider when the sheath slider is adjacent the string control slider wherein the string control slider further comprises a hard stop and one or more string control slider detent arms in an interior of the user interface and a rib.

Another aspect of the disclosure is directed to methods of inserting an IUD into a uterus with an insertion device. Suitable methods comprise the steps of: providing the insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, a rail along a side of the moveable sheath slider and a lateral detent arm, and a string control slider having a curved distal surface for abutting with the curved surface of the moveable sheath slider when the sheath slider is adjacent the string control slider wherein the string control slider further comprises a hard stop and one or more string control slider detent arms in an interior of the user interface and a rib; advancing the insertion device and the IUD into the uterus; actuating the sheath slider of the insertion device; at least one of moving the elongated sheath proximally and advancing the IUD distally; automatically or semi-automatically increasing a radial diameter of the IUD; and releasing the IUD from the insertion device.

Still another aspect of the disclosure is directed to methods of hormonally treating a patient. Suitable methods comprise the steps of: providing an IUD which delivers an active agent; inserting the IUD with the active agent into a uterus of a patient with an insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, a rail along a side of the moveable sheath slider and a lateral detent arm, and a string control slider having a curved distal surface for abutting with the curved surface of the moveable sheath slider when the sheath slider is adjacent the string control slider wherein the string control slider further comprises a hard stop and one or more string control slider detent arms in an interior of the user interface and a rib; advancing the insertion device and the IUD with the active agent into the uterus; actuating the sheath slider of the insertion device; at least one of moving the elongated sheath proximally and advancing the IUD with the active agent distally; releasing the IUD with the active agent from the insertion device; and delivering the active agent from the IUD to the patient.

Another aspect of the disclosure is directed to insertion devices for inserting an IUD comprising: an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, a rail along a side of the moveable sheath slider and a lateral detent arm, and a string control slider having a curved distal surface for abutting with the curved surface of the moveable sheath slider when the sheath slider is adjacent the string control slider. In some configurations, the proximally positioned user interface and the sheath slider further comprise one or more alignment surfaces, wherein the one or more alignment surfaces of the user interface is adapted and configured to mechanically complement the one or more alignment surfaces of the sheath. Additionally, a first sheath slider alignment surface can align with a first user interface alignment surface at a first position along a length of the elongated channel. The elongated channel can further comprise one or more cavities on one or more of a proximal end of the elongated channel and a distal end of the elongated channel wherein the one or more cavities are adapted and configured to house at least a portion of the movable sheath slider. The string control slider can be configured such that it is adaptable and configurable to securely move within the elongated channel. In at least some configurations, the moveable sheath slider and the string control slider are adapted and configured to operate at least one of simultaneously and independently within the elongated channel. The string slider can also be configured to partially surround and the sheath slider. The insertion device can be configurable to receive the IUD within a distal end of the lumen of the elongated sheath and wherein the insertion device further comprises at least one string locking feature adaptable and configurable to secure one or more string components of the IUD. Additionally, the distal end of the elongated sheath can have an atraumatic tip selected from the group comprising a rounded tip and a tapered tip. The moveable sheath slider can further comprise a second rail along a second side of the moveable sheath slider and a second lateral detent arm. Additionally, in at least some configurations, the moveable sheath slider further comprises a top half and a bottom half. The string control slider further can further comprise an interiorly positioned hard stop. The user interface can further comprise one or more string control slider detent arm in an interior of the user interface and a rib. In some configurations, the one or more string control slider detent arms flex inwardly and/or flex outwardly, i.e, towards a central axis or away from a central axis.

Still another aspect of the disclosure is directed to methods of inserting an IUD into a uterus with an insertion device comprising the steps of: providing the insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath, an elongated inner member having a proximal end and a distal end disposable within the lumen of the elongated sheath wherein a proximal end of the IUD is positionable adjacent the distal end of the elongated inner member, a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, a rail along a side of the moveable sheath slider and a lateral detent arm, and a string control slider having a curved distal surface for abutting with the curved surface of the moveable sheath slider when the sheath slider is adjacent the string control slider; advancing the insertion device and the IUD into the uterus; actuating the sheath slider of the insertion device; at least one of moving the elongated sheath proximally and advancing the IUD distally; automatically or semi-automatically increasing a radial diameter of the IUD; and releasing the IUD from the insertion device. The methods can further comprise the step of moving the string control slider within the elongated channel. Additionally, the step of moving the moveable sheath slider and the string control slider of the insertion device can occur simultaneously within the elongated channel. In some embodiments, the step of moving the moveable sheath slider and the string control slider of the insertion device independently within the elongated channel. The sheath slider and the string control slider of the insertion device can also be moved telescopically along at least a first portion of the elongated channel. The IUD can deliver an active agent once inserted. The active agent can be a hormone used for the treatment of menopausal troubles or for contraception.

Yet another aspect of the disclosure is directed to methods of hormonally treating a patient comprising the steps of: providing an IUD which delivers an active agent; inserting the IUD with the active agent into a uterus of a patient with an insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath, an elongated inner member having a proximal end and a distal end disposable within the lumen of the elongated sheath wherein a proximal end of the IUD is positionable adjacent the distal end of the elongated inner member, a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, a rail along a side of the moveable sheath slider and a lateral detent arm, and a string control slider having a curved distal surface for abutting with the curved surface of the moveable sheath slider when the sheath slider is adjacent the string control slider; advancing the insertion device and the IUD with the active agent into the uterus; actuating the sheath slider of the insertion device; at least one of moving the elongated sheath proximally and advancing the IUD with the active agent distally; releasing the IUD with the active agent from the insertion device; and delivering the active agent from the IUD to the patient. The active agent can be a hormone used for the treatment of menopausal troubles or for contraception.

Another aspect of the disclosure is directed to an insertion device for inserting an IUD comprising: an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, and a string control slider having a curved distal surface for abutting with the curved surface of the moveable sheath slider when the sheath slider is adjacent the string control slider wherein the string control slider further comprises an interiorly positioned hard stop. The proximally positioned user interface and the sheath slider can further comprise one or more alignment surfaces, wherein the one or more alignment surfaces of the user interface is adapted and configured to mechanically complement the one or more alignment surfaces of the sheath. In some configurations, a first sheath slider alignment surface aligns with a first user interface alignment surface at a first position along a length of the elongated channel. The elongated channel further comprises one or more cavities on one or more of a proximal end of the elongated channel and a distal end of the elongated channel wherein the one or more cavities are adapted and configured to house at least a portion of the movable sheath slider. In some configurations, the string control slider is adaptable and configurable to securely move within the elongated channel. Additionally, the moveable sheath slider and the string control slider are adapted and configured in at least some configurations to operate at least one of simultaneously and independently within the elongated channel. The string slider can be configured to partially surround and the sheath slider in some configurations. The insertion device can be configurable to receive the IUD within a distal end of the lumen of the elongated sheath and further comprise at least one string locking feature adaptable and configurable to secure one or more string components of the IUD. The distal end of the elongated sheath can be configurable to have an atraumatic tip selected from the group comprising a rounded tip and a tapered tip. In some configurations, the moveable sheath slider further comprises a rail along a side of the moveable sheath slider and a lateral detent arm. The moveable sheath slider can further comprise a second rail along a second side of the moveable sheath slider and a second lateral detent arm. The moveable sheath slider can further comprise a top half and a bottom half in some configurations. Additionally, the user interface can further comprise one or more string control slider detent arm in an interior of the user interface and a rib. The one or more string control slider detent arms can also be configured to flex inwardly and/or flex outwardly.

Still another aspect of the disclosure is directed to methods of inserting an IUD into a uterus with an insertion device comprising the steps of: providing the insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, and a string control slider having a curved distal surface for abutting with the curved surface of the moveable sheath slider when the sheath slider is adjacent the string control slider wherein the string control slider further comprises an interiorly positioned hard stop; advancing the insertion device and the IUD into the uterus; actuating the sheath slider of the insertion device; at least one of moving the elongated sheath proximally and advancing the IUD distally; automatically or semi-automatically increasing a radial diameter of the IUD; and releasing the IUD from the insertion device. The methods can further comprise the step of moving the string control slider within the elongated channel. Additionally, the step of moving the moveable sheath slider and the string control slider of the insertion device can occur simultaneously within the elongated channel. In some embodiments, the step of moving the moveable sheath slider and the string control slider of the insertion device independently within the elongated channel. The sheath slider and the string control slider of the insertion device can also be moved telescopically along at least a first portion of the elongated channel. The IUD can deliver an active agent once inserted. The active agent can be a hormone used for the treatment of menopausal troubles or for contraception.

Another aspect of the disclosure is directed to methods of hormonally treating a patient comprising the steps of: providing an IUD which delivers an active agent; inserting the IUD with the active agent into a uterus of a patient with an insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, and a string control slider having a curved distal surface for abutting with the curved surface of the moveable sheath slider when the sheath slider is adjacent the string control slider wherein the string control slider further comprises an interiorly positioned hard stop; advancing the insertion device and the IUD with the active agent into the uterus; actuating the sheath slider of the insertion device; at least one of moving the elongated sheath proximally and advancing the IUD with the active agent distally; releasing the IUD with the active agent from the insertion device; and delivering the active agent from the IUD to the patient. The active agent can be a hormone used for the treatment of menopausal troubles or for contraception.

Another aspect of the disclosure is directed to insertion device for inserting an IUD comprising: an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, and a string control slider having a curved distal surface for abutting with the curved surface of the moveable sheath slider when the sheath slider is adjacent the string control slider wherein the string control slider further comprises one or more string control slider detent arms in an interior of the user interface and a rib. The proximally positioned user interface and the sheath slider can further comprise one or more alignment surfaces, wherein the one or more alignment surfaces of the user interface is adapted and configured to mechanically complement the one or more alignment surfaces of the sheath. Additionally, a first sheath slider alignment surface can align with a first user interface alignment surface at a first position along a length of the elongated channel. The elongated channel can further comprise one or more cavities on one or more of a proximal end of the elongated channel and a distal end of the elongated channel wherein the one or more cavities are adapted and configured to house at least a portion of the movable sheath slider. The string control slider, in some configurations, is adaptable and configurable to securely move within the elongated channel. The moveable sheath slider and the string control slider are also adaptable and configurable to operate at least one of simultaneously and independently within the elongated channel. The string slider can also be configured to partially surrounds and the sheath slider. In some configurations, the insertion device is configurable to receive the IUD within a distal end of the lumen of the elongated sheath and wherein the insertion device further comprises at least one string locking feature adaptable and configurable to secure one or more string components of the IUD. The distal end of the elongated sheath can have an atraumatic tip selected from the group comprising a rounded tip and a tapered tip. Additionally, the moveable sheath slider can further comprise a second rail along a second side of the moveable sheath slider and a second lateral detent arm. In some configurations, the moveable sheath slider further comprises a top half and a bottom half. The moveable sheath slider further comprises a rail along a side of the moveable sheath slider and a lateral detent arm. The user interface can further comprise a hard stop. Additionally, one or more string control slider detent arms can flex inwardly and/or flex outwardly.

Still another aspect of the disclosure is directed to methods of inserting an IUD into a uterus with an insertion device comprising the steps of: providing the insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, and a string control slider having a curved distal surface for abutting with the curved surface of the moveable sheath slider when the sheath slider is adjacent the string control slider wherein the string control slider further comprises one or more string control slider detent arms in an interior of the user interface and a rib; advancing the insertion device and the IUD into the uterus; actuating the sheath slider of the insertion device; at least one of moving the elongated sheath proximally and advancing the IUD distally; automatically or semi-automatically increasing a radial diameter of the IUD; and releasing the IUD from the insertion device. The methods can further comprise the step of moving the string control slider within the elongated channel. Additionally, the step of moving the moveable sheath slider and the string control slider of the insertion device can occur simultaneously within the elongated channel. In some embodiments, the step of moving the moveable sheath slider and the string control slider of the insertion device independently within the elongated channel. The sheath slider and the string control slider of the insertion device can also be moved telescopically along at least a first portion of the elongated channel. The IUD can deliver an active agent once inserted. The active agent can be a hormone used for the treatment of menopausal troubles or for contraception.

Yet another aspect of the disclosure is directed to methods of hormonally treating a patient comprising the steps of: providing an IUD which delivers an active agent; inserting the IUD with the active agent into a uterus of a patient with an insertion device wherein the insertion device comprises an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; a proximally positioned user interface, wherein the proximally positioned user interface further comprises an elongated channel, a moveable sheath slider moveable within the elongated channel wherein the moveable sheath slider has an upper surface, a lower surface and two side surfaces, further wherein the moveable sheath slider has a depression on an upper surface of the moveable sheath slider facing an exterior of the user interface, and a string control slider having a curved distal surface for abutting with the curved surface of the moveable sheath slider when the sheath slider is adjacent the string control slider wherein the string control slider further comprises one or more string control slider detent arms in an interior of the user interface and a rib; advancing the insertion device and the IUD with the active agent into the uterus; actuating the sheath slider of the insertion device; at least one of moving the elongated sheath proximally and advancing the IUD with the active agent distally; releasing the IUD with the active agent from the insertion device; and delivering the active agent from the IUD to the patient. The active agent can be a hormone used for the treatment of menopausal troubles or for contraception.

INCORPORATION BY REFERENCE

All publications, patents, and patent applications mentioned in this specification are herein incorporated by reference to the same extent as if each individual publication, patent, or patent application was specifically and individually indicated to be incorporated by reference.

U.S. Pat. No. 3,407,806 A to Hulka et al. for Contraceptive Intra-Uterine Devices issued Oct. 29, 1968;

U.S. Pat. No. 3,783,861 A to Abramson for Inserter for Intrauterine Devices issued Jan. 8, 1974;

U.S. Pat. No. 3,794,025 A to Lerner for Intrauterine Device Saddle Inserter issued Feb. 26, 1974;

U.S. Pat. No. 3,902,483 A to Place et al. for Intrauterine Device with Locator Means for Indicating Uterine Position of Device issued Sep. 2, 1975;

U.S. Pat. No. 3,937,217 A to Kosonen for Intrauterine Contraceptive Device issued Feb. 10, 1976;

U.S. Pat. No. 4,353,363 A to Quesada for Intrauterine Spermicide issued Oct. 12, 1982;

U.S. Pat. No. 4,359,046 A to Shaw Jr. for IUD Arrangement issued Nov. 16, 1982;

U.S. Pat. No. 4,372,302 A to Akerlund for Instrument for Retrieval of Retracted Threads of Intrauterine Contraceptive Devices issued Feb. 8, 1983;

U.S. Pat. No. 4,381,001 A to Shaw Jr. for IUD Arrangement issued Apr. 26, 1983;

U.S. Pat. No. 4,495,934 A to Shaw Jr. for IUD Arrangement issued Jan. 29, 1985;

U.S. Pat. No. 4,830,025 A to Gainutdinova et al. for Intrauterine Contraceptive Device issued May 16, 1989;

U.S. Pat. No. 4,920,727 A to Ristimaki et al. for Cassette System and Apparatus for Manufacturing an Active Agent Liberating Capsule for Subcutnaeous Use issued May 1, 1990;

U.S. Pat. No. 4,949,732 A to Spoon et al. for Apparatus for Insertion and Fixation of an Intra Uterine Contraceptive Device to the Uterine Fundus issued Aug. 21, 1990;

U.S. Pat. No. 4,957,119 A to de Nijs for Contraceptive Implant issued Sep. 18, 1990;

U.S. Pat. No. 5,084,004 A to Ranoux for Process for Intra-Uterine Fertilization in Mammals and Device for Implementation Thereof issued Jan. 28, 1992;

U.S. Pat. No. 5,088,505 A to de Nijs for Contraceptive Implant issued Feb. 18, 1992;

U.S. Pat. No. 5,370,129 A to Diaz et al. for IUD Inserting Apparatus issued Dec. 6, 1994;

U.S. Pat. No. 5,400,804 A to Helle et al. for Method and Equipment for Installing a Medicine Capsule on a Support issued Mar. 28, 1995;

U.S. Pat. No. 5,785,053 A to Macandrew et al. for Inserter for the Positioning of an Intrauterine Device issued Jul. 28, 1998;

U.S. Pat. No. 6,039,968 A to Nabahi for Intravaginal Drug Delivery Device issued Mar. 21, 2000;

U.S. Pat. No. 6,056,976 A to Markkula et al. for Elastomer, Its Preparation and Use issued May 2, 2000;

U.S. Pat. No. 6,063,395 A to Markkula et al. for Drug Delivery Device Especially for the Delivery of Progestins and Estrogens issued May 16, 2000;

U.S. Pat. No. 6,103,256 A to Nabahi for Intravaginal Drug Delivery Device issued Aug. 15, 2000;

U.S. Pat. No. 6,117,442 A to Markkula et al. for Drug Delivery Device, Especially for the Delivery of Androgens issued Sep. 12, 2000;

U.S. Pat. No. 7,862,552 B2 to McIntyre et al. for Medical Devices for Treating Urological and Uterine Conditions issued Jan. 4, 2011;

U.S. Pat. No. 10,028,858 B2 to Deckman et al. for Intrauterine Systems, IUD Insertion Devices, and Related Methods and Kits Therefor issued Jul. 24, 2018;

U.S. Patent Pub. US 2005/0045183 A1 to Callister et al. for Methods and Devices for Occluding Body Lumens and/or for Delivering Therapeutic Agents issued Mar. 3, 2005; and U.S. Patent Pub. US 2008/0095825 A1 to LaFont for Method for Making a Reservoir Containing an Active Substance Diffused Through the Reservoir and Installation Therefor published Apr. 24, 2008.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates a demonstrator (representing a portion of the female anatomy) with an IUD positioned within a portion corresponding to a cervical canal, FIG. 3B illustrates an IUD positioned within a distal end of a sheath, FIG. 3C illustrates another cross-section of an IUD positioned within a distal end of a sheath, and FIG. 3D illustrates a view down the barrel from the distal end of the IUD and sheath;

FIG. 7A illustrates a first embodiment of a sheath slider;

FIG. 7B illustrates a second embodiment of a sheath slider;

FIG. 7C illustrates the first embodiment of a sheath slide positioned within an interior of insertion device handle in a first configuration;

FIG. 7D illustrates the first embodiment of a sheath slide positioned within an interior of insertion device handle in a second configuration;

FIG. 8 illustrates a portion of the string control slider and the insertion device handle;

FIG. 9 illustrates portion of the insertion device handle with a sheath slider positioned underneath a string control slider;

FIG. 10 illustrates a portion of a cross-section of the elongated sheath with an IUD positioned therein;

FIG. 11 illustrates an interior of a portion of the distal end of the insertion device handle;

FIG. 12A illustrates an interior portion of the distal end of the insertion device with the sheath slider detents engaging detents in a first configuration at a first position;

FIG. 12B illustrates an interior portion of the distal end of the insertion device with the sheath slider detent and detent in a second configuration at a first position;

FIG. 12C illustrates an interior portion of the insertion device with ribs engaging detents at a second position;

FIG. 12D illustrates an interior portion of the insertion device with the string control slider detents at a third position;

FIG. 12E illustrates an interior portion of the insertion device with the string control slider detents at a third position;

FIG. 13A illustrates an interior view of a first configuration of a sheath slider;

FIG. 13B illustrates an interior view of a second configuration of a sheath slider;

FIG. 13C illustrates an interior view of a third configuration of a sheath slider;

FIG. 14 illustrates a portion of the insertion device handle showing the interface between the top and bottom halves;

FIG. 15 illustrates a cut-away portion of an insertion device handle with a string control surface;

FIG. 16 illustrates a string control slider; and

FIGS. 17A-C illustrate the proximal and distal end of the insertion device at phase 1 of the insertion process (FIG. 17A), phase 2 of the insertion process (FIG. 17B) and phase 3 of the insertion process (FIG. 17C).

DETAILED DESCRIPTION

I. Insertion Procedure

Figures 1A, 1B, 1C:
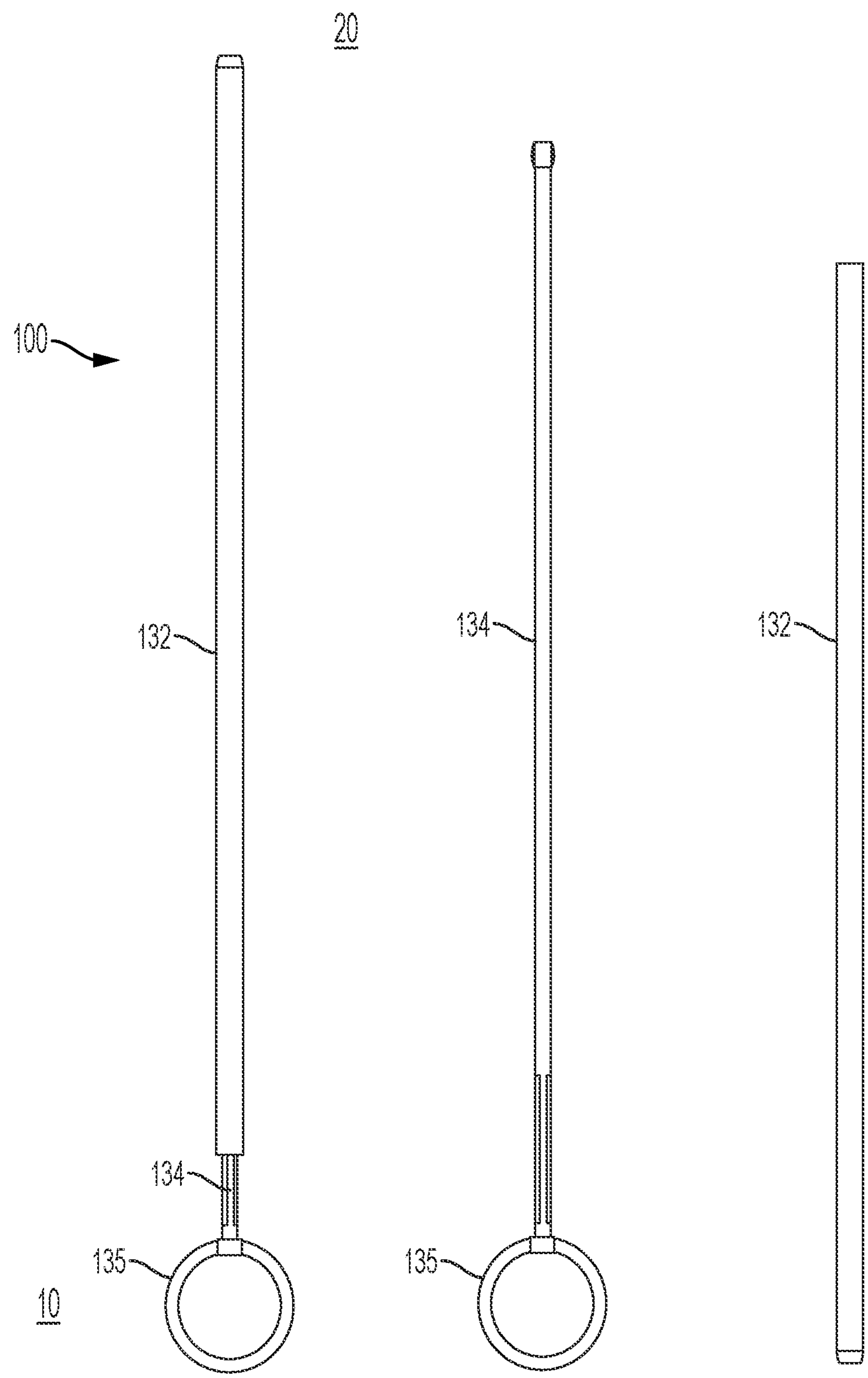
FIGS. 1A-1C illustrate a conventional two-handed IUD insertion device.

One type of intrauterine insertion devices is a two-handed insertion device 100 or inserter such as the two-handed insertion device 100 shown in FIGS. 1A-1C. The two-handed insertion device 100 includes a sheath 132 having a proximal end 10 and a distal end 20 and a lumen extending between the proximal end and the distal end for housing the IUD. A plunger 134 is provided for pushing and IUD through the sheath when deploying the IUD within a uterus of a patient. User interface, such as a handle 135, is provided for holding the two-handed insertion device 100. When in use, an operator (healthcare provider) holds the handle 135 of the two-handed insertion device shown in FIGS. 1A-1C in one hand and the sheath 132 with the other hand. When the insertion device is positioned within the uterus of a patient, the handle 135 is moved distally to push the IUD, which is positioned within the sheath 132, out the distal end of the sheath 132. Once the IUD is pushed out of the distal end of the sheath, the IUD is deployed within the uterus of the patient.

As will be discussed in more detail below, in contrast to two-handed insertion devices, such as depicted in FIG. 1A-C, the insertion devices of the present disclosure are configured to house an IUD during the insertion procedure and is further configured to aid in positioning the IUD during the insertion procedure as well as advancing the IUD from the insertion device into a patient's uterus. The insertion devices are adaptable and configurable for insertion of a variety of IUDs configurations. Moreover, the insertion devices can be operated with a single hand. The insertion devices also provide tactile feedback to the user during the insertion steps.

Figure 2:
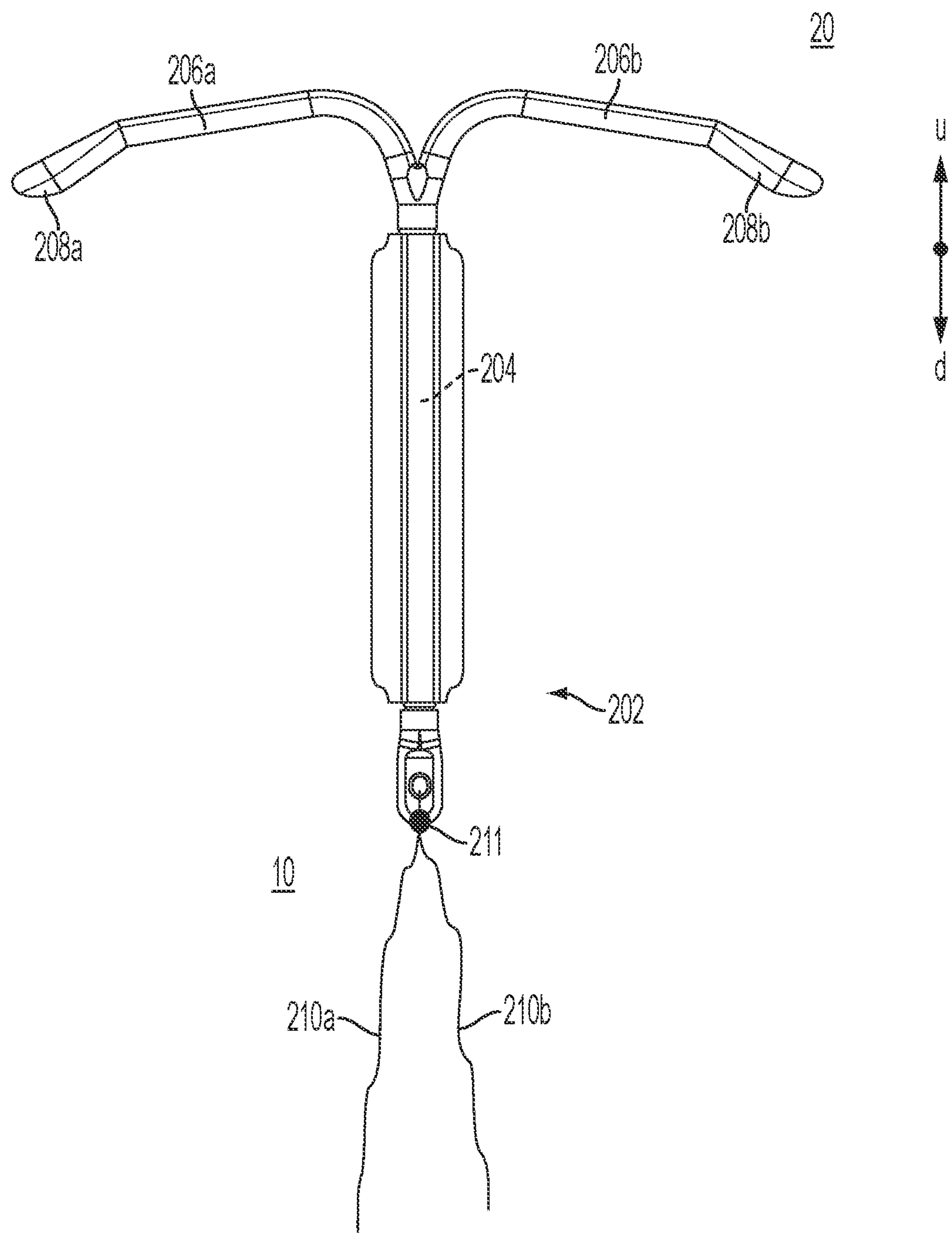
FIG. 2 illustrates a conventional t-shaped IUD.

The insertion devices can, for example, be used with a t-shaped IUD 202, such as the IUD as shown in FIG. 2. IUDs typically have a length of from about 31.90 mm to about 32.22 mm and a width of from about 31.81 mm to about 32.13 mm when the IUD is in the fully deployed position. As will be appreciated by those skilled in the art, the length does not include the knot or strings that may accompany the IUD. The t-shaped IUD comprises an elongated body 204 having a proximal end 10 and a distal end 20. The elongated body 204 can include a coating such as a time-release drug or hormone. The elongated body 204 can be formed from any suitable material, including, but not limited to plastic or copper. At the distal end 20 of the IUD (i.e., the end positioned away from the physician's hand), IUD arms 206*a*, 206*b* are attached to or integrally formed with the elongated body 204. The IUD arms 206*a*, 206*b* are configurable to fold upward u or downward d to minimize the IUD cross-section such that the IUD can fit into an insertion device sheath or tube for insertion through the cervix and into the uterus. Additionally, either or both of the IUD arms 206*a*, 206*b* are configurable to include an enlarged or bulbous tips 208*a*, 208*b*, which can, for example, have a curved, spherical or semi-spherical shape. The bulbous tips 208*a*, 208*b* of the IUD arms 206*a*, 206*b* can be formed such that the IUD arms, when folded upward and pushed together, form a smooth and rounded distal tip, for example, as shown in FIGS. 3B-3C and described below. At the proximal end of the t-shaped IUD 202, the IUD can further include one or more strings 210*a*, 210*b* attached to the IUD. The strings are connectable to the IUD at a connection point 211, e.g., tied in a knot as illustrated.

Although the insertion devices are generally described herein with regard to a t-shaped IUD such as the IUD shown in FIG. 2, it should be noted that the insertion devices of the present disclosure are adaptable to facilitate insertion of other IUD configurations, as would be appreciated by a person of skill in the art. Moreover, insertion device operation and IUD insertion procedures can include any number of steps corresponding to a desired IUD position. In addition to the features described below, the insertion devices of the present disclosure include IUD position control features which may be advantageous for insertion of IUDs having a variety of configurations. For example, while the IUD insertion procedure described below refers to a three-phase procedure corresponding to three different IUD positions, the insertion device operation procedure can include less than three or more than three steps. Accordingly, the insertion devices can include any number of position control features corresponding to the desired IUD positions. The insertion device of the present disclosure can be used with various conventional IUDs available on the market, including such devices as the T-frame LNg-20 IUD, marketed as Mirena® by Bayer®, as well as the Neo-Safe CuT 380A™ available from Mona-Lisa™.

Insertion devices disclosed herein are configurable to operate according to procedural steps which generally mimic commonly known and used procedures for IUD insertion. However, the insertion devices of the present disclosure include improvements in the structure and operation of the insertion devices. In another aspect of the disclosed insertion devices, procedural steps for IUD insertion include: (i) insertion device preparation procedures that occur pre-insertion, (ii) a first phase of IUD insertion (also referred to herein as phase 1, position 1, or step 1), (iii) a second phase of IUD insertion (also referred to herein as phase 2, position 2, or step 2), (iv) a third phase of IUD insertion (also referred to herein as phase 3, position 3, or step 3), and (v) post-insertion procedures. The positioning and operation of the insertion devices during the first phase through third phase are discussed in more detail below with respect to FIGS. 17A-17C.

Insertion device preparation procedures that occur pre-insertion include, for example, loading a t-shaped IUD 202, such as the IUD illustrated in FIG. 2, into an insertion device, aligning the t-shaped IUD 202 in-plane with a patient, positioning the t-shaped IUD 202 in a correct longitudinal position along the length of a sheath of the insertion device, and locking the IUD into a position for insertion. As will be appreciated by those skilled in the art, loading the IUD into the insertion device can occur as part of Such insertion device preparation procedures are described in further detail below.

Figure 3A:
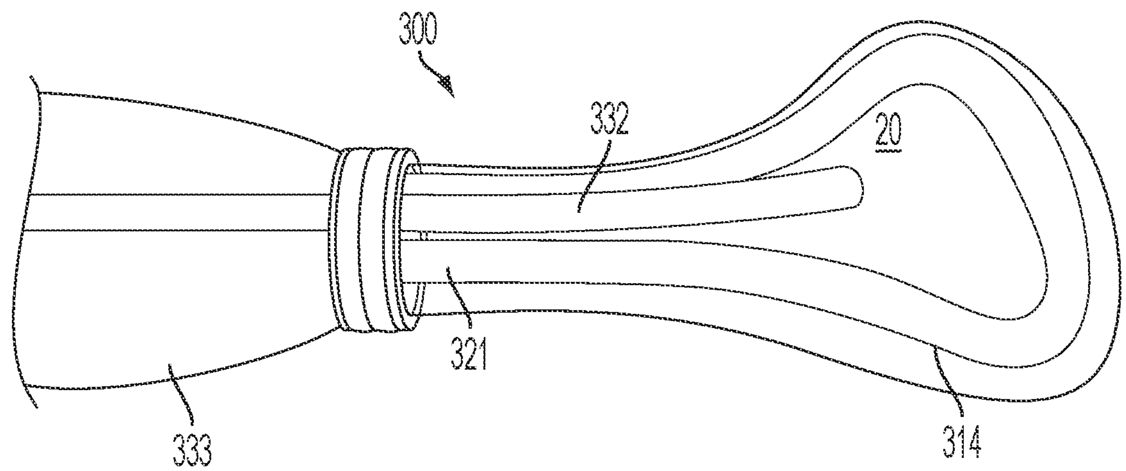
FIGS. 3A-3D illustrate positioning of an IUD during the first phase of IUD insertion.
Figure 3B:
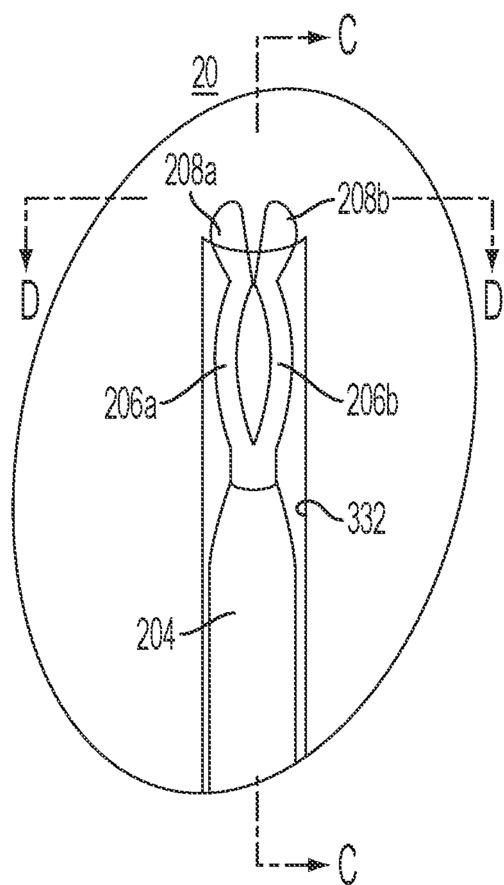
Figure 3C:
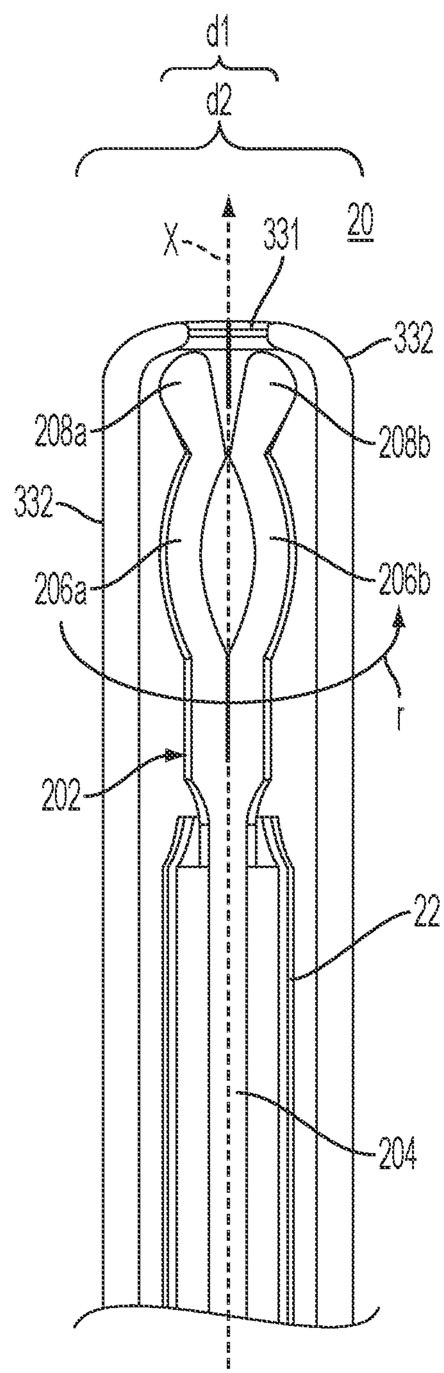

FIGS. 3A-3C illustrate positioning of the distal tip of an insertion device 300 during a first phase of IUD insertion according to an aspect of the present disclosure using a demonstrator 333 to represent patient anatomy. The demonstrator 333 has a cervical canal 321 area and a uterus 314 area.

In FIG. 3A, the insertion device 300 is sized and configured for positioning within a uterus, having a tube length (or working length) of from 15 cm to 25 cm, and a diameter of 3 mm to about 5 mm. A distal end 20 of a sheath 332, having a proximal end and a distal end and a sheath lumen extending between the proximal end and the distal end, is advanced through a cervical canal such that the sheath 332 protrudes slightly into the uterus (uterus 314 area of the demonstrator 333). The t-shaped IUD 202 is not yet deployed and remains within the sheath 332. The bulbous tips 208*a*, 208*b* of the t-shaped IUD 202 may be partially deployed to create a rounded shape at the distal end 20 of the insertion device 300, as shown in FIG. 3B, while the elongated body 204 of the t-shaped IUD 202 remains positioned within the elongated lumen of the sheath 332 Alternatively, in aspects where the sheath 332 of the insertion device 300 or other feature provides a rounded distal tip, the IUD arms 206*a*, 206*b* are encasable by the sheath 332, as shown in the cross-section taken along the lines B-B in FIG. 3B and shown in FIG. 3C. In a first dimension, the diameter of the IUD when it is fully positioned within the sheath 332 will be smaller than a second, larger, diameter when the IUD is advanced distally beyond the tip of the sheath 332 so that the IUD arms 206*a*, 206*b* extend away from a central axis of the t-shaped IUD 202. A reservoir 220 can be provided for containing an active agent.

Figure 3D:
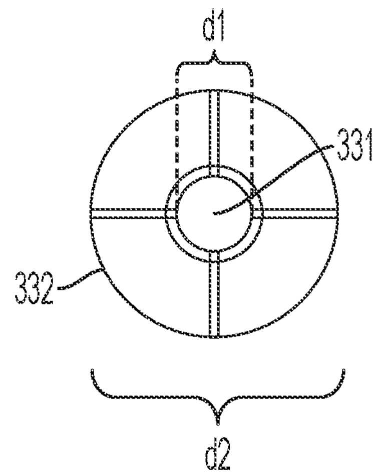

FIG. 3D illustrates a view down the barrel of the device taken from the view D-D in FIG. 3B of the insertion device 300, during a first phase of IUD insertion according to an aspect of the present disclosure. Aperture 331 has a diameter d1 that is smaller than the diameter d2 of the sheath 332. The t-shaped IUD 202 is rotatable r in-plane about longitudinal axis x as shown in FIG. 3D, such that the IUD arms 206*a*, 206*b*, or similar features of the IUD will deploy in-line with respective openings of the patient's fallopian tubes.

A contraceptive device, which is available on the market and which releases levonorgestrel, consists of a t-shaped IUD 202 having an elongated body 204 fabricated of polyethylene equipped with a reservoir 220 adjusted around the elongated body 204 and containing, for example, the hormone levonorgestrel. Thus, the IUD is configurable to comprise a core part around which a jacket-like polymeric reservoir containing an active agent has been fitted. The active agent includes hormones used for the treatment of menopausal troubles or for contraception. The IUD is sold in sterile packaging together with the inserter with the plunger contained within the protecting tube. The t-shaped IUD 202 can be positioned at the forward end of the plunger (distal end) with the hormone-containing elongate member protected by the sheath 132. The IUD arms 206*a*, 206*b* of the transverse member, on the other hand, are expanded in order to prevent fatigue. The strings 210*a*, 210*b* by which the t-shaped IUD 202 is retracted towards the outside of a patient during removal (e.g., pulled proximally) run between the plunger 134 and the sheath 132 (e.g., protective tube) and end at the end of the handle 135.

Figure 4C:
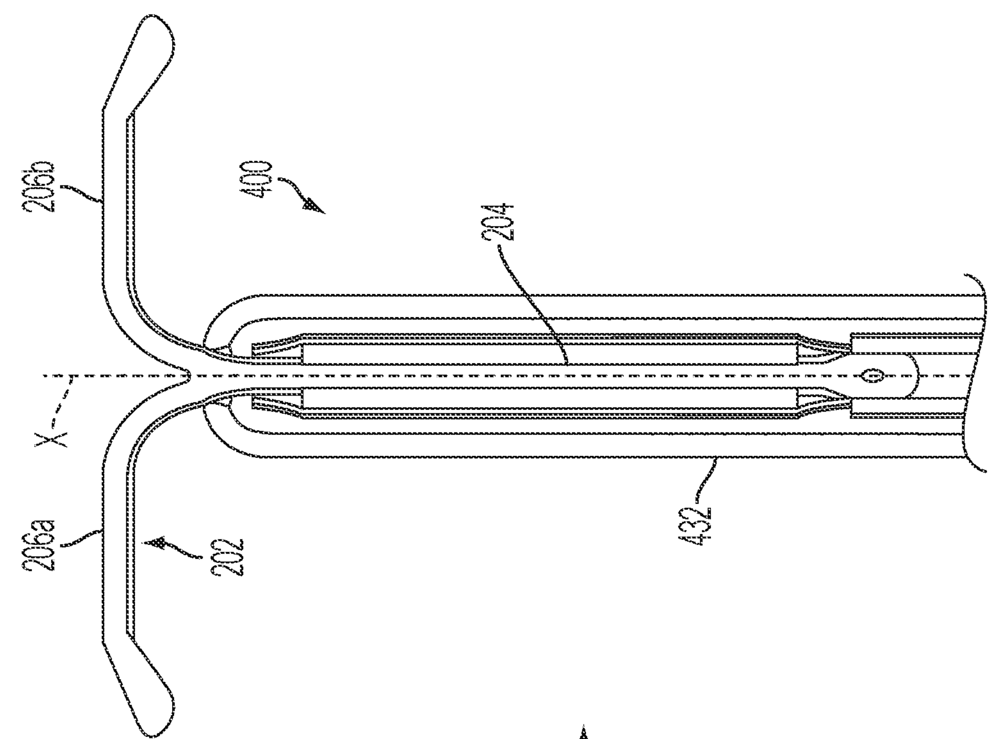
FIGS. 4A-4C illustrate positioning of an IUD within an insertion device during transition from a first phase of an IUD insertion process where the IUD arms are fully positioned within the distal end of the sheath (FIG. 4A), begin to extend from the distal end of the sheath (FIG. 4B) and are fully extended beyond the distal end of the sheath (FIG. 4C)
Figure 4B:
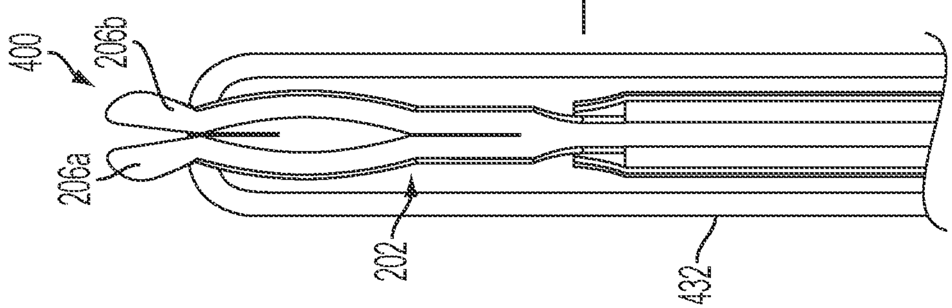
Figure 4A:
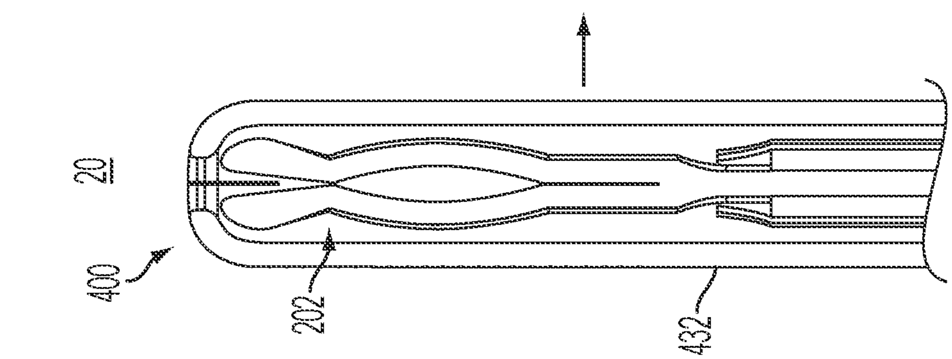

FIGS. 4A-4C depict a cross-section of the t-shaped IUD 202 positioned in a distal end 20 of an insertion device 400 taken along the lines 4-4 of FIG. 3B. Initially, the t-shaped IUD 202 is fully positioned within the sheath 432 of the insertion device (FIG. 4A during phase 1). Once the insertion device is positioned within the uterus, the t-shaped IUD 202 is advanced distally so that the IUD arms 206*a*, 206*b* begin to exit the sheath 432 of the insertion device 400 (FIG. 4B during phase 1).

Once the IUD is advanced distally the IUD arms 206*a*, 206*b* of the t-shaped IUD 202 extend radially away from a central axis x when the IUD arms 206*a*, 206*b* are clear of the distal end of the sheath during phase 2 of the insertion process.

Figure 4D:
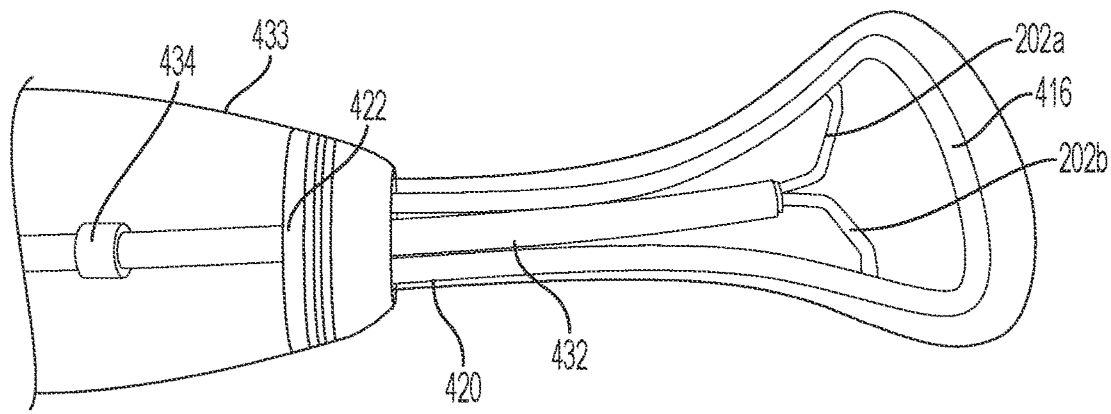
FIGS. 4D-4E illustrate positioning of an IUD within an insertion device through the second phase of IUD insertion, wherein the IUD arms engage the side walls of the demonstrator (FIG. 4D) which represents the uterus, and where the IUD is extended towards the far wall of the demonstrator (FIG. 4E) which represents the fundus.
Figure 4E:
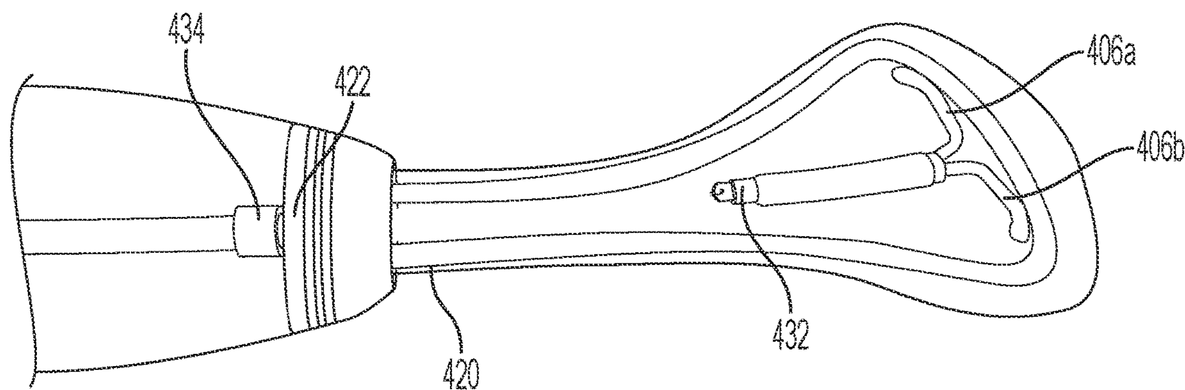

FIGS. 4D-4E illustrate positioning of an insertion device 400 during phase 2 of the IUD insertion procedure using a demonstrator 433 to represent the patient anatomy. The t-shaped IUD 202 is partially deployed (similar to FIG. 4C) such that the elongated body 204 of the t-shaped IUD 202 remains positioned within the sheath 432, and the IUD arms 206*a*, 206*b* of the t-shaped IUD have been fully released from the sheath 432 and unfold to extend outward from the elongated body 204 of the t-shaped IUD 202. As shown in FIG. 4D, the insertion device 400 is extended distally into the uterus, represented by the demonstrator 433, until a flange 434 reaches a set distance from an external orifice 422 of the cervix 420, and the IUD is partially deployed from the sheath 432 of the insertion device 400 into the uterus. A clinician operating the insertion device 400 can, during use, maintain a position shown in FIG. 4D for a period of time, e.g., 10-25 seconds, and more often 15 seconds, to ensure that the IUD arms 206*a*, 206*b* of the t-shaped IUD are fully unfolded or expanded to the desired position or configuration. Subsequently, as shown in FIG. 4E, the insertion device 400 is advanced distally until the flange 434 reaches the external orifice of the cervix 420, at which point the IUD arms 206*a*, 206*b* of the t-shaped IUD 202 contact the fundus 416 of the uterus.

Figure 5A:
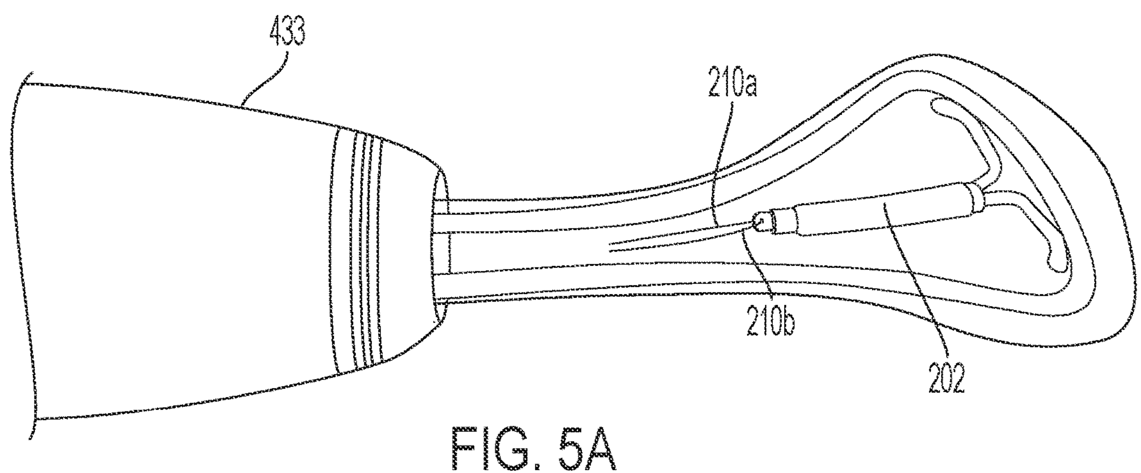
FIG. 5A illustrates positioning of an IUD with the IUD arms engaging the side walls of the demonstrator.
Figure 5B:
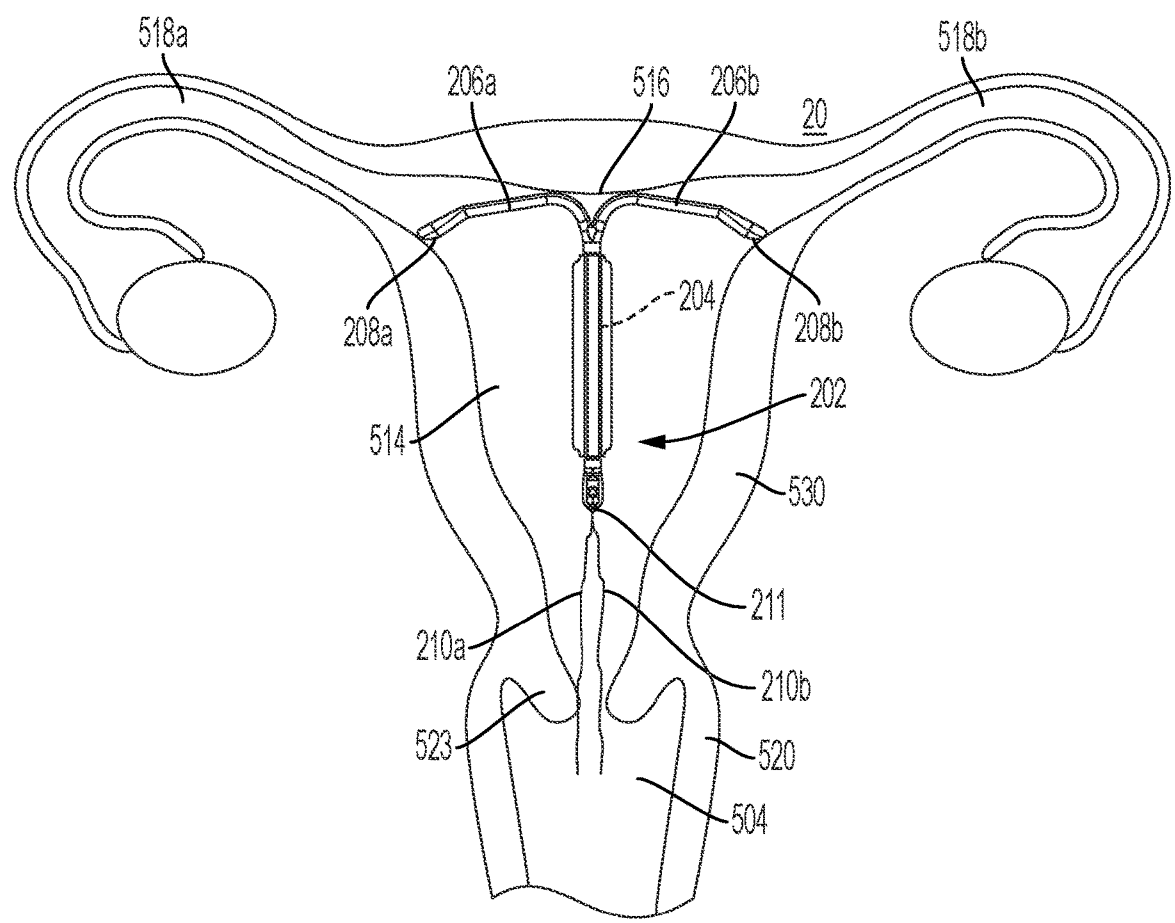
FIG. 5B illustrates an IUD deployed from the insertion device within the interior of the uterus.

FIGS. 5A-5B illustrate positioning of a t-shaped IUD 202 during phase 3 of an insertion procedure. The t-shaped IUD 202 is completely deployed from the insertion device into the uterus (shown as the demonstrator 433 in FIG. 5A).

FIG. 5B provides a planar view showing a detailed illustration of the relevant female anatomy, including the uterus 514, fundus 516, openings of the fallopian tubes 518*a*, 518*b*, cervix 520, cervical canal 521, external orifice 522 of the cervix 520, and internal orifice 523 of the cervix 520. Once inserted, the IUD strings 210 extend from the uterus 514, through the cervix 520, and into the vagina 524, as shown in FIG. 5B.

Upon completion of the IUD insertion phase, post-insertion procedures can be performed, such as removal of the insertion device sheath from the patient and trimming the IUD strings to an appropriate length for a particular patient.

The insertion devices of the present disclosure demonstrate improved device structure and operation technique, as well as increased ease of operability for the user. The insertion devices of the present disclosure are configured to reduce pain and trauma suffered by patients during the IUD insertion procedure. Most women have a cervix which varies in diameter of the opening from about 1 to about 3 millimeters. The size and shape of the cervix varies widely with the patient's age, the patient's hormonal state, and whether the patient has born a child via vaginal birth. However, the IUD and insertion device typically have a diameter larger than the diameter of the cervical canal, especially at the external orifice and internal orifice of the cervix or uterus. Such a mismatch between the diameters of the cervix and insertion device creates a resistive pathway for IUD insertion which can hinder proper insertion of the IUD and result in a traumatic insertion for the patient. Diameters of IUDs and traditional insertion devices are large compared to the typical female human cervical canal into which the IUD and applicator are inserted during the IUD insertion process. As will be appreciated by those skilled in the art, traumatic IUD insertion procedures can cause a variety of adverse side effects including, but not limited to, bleeding, intense pain, and an adverse vasovagal response, which can result in fainting or seizure.

Pain during the IUD insertion procedure is reduced by the structure and operation of the insertion device, as well as by the ease of operability of the insertion device. Traumatic insertion can result from difficulties in operating the IUD insertion tool, malfunctioning of the insertion device, improper IUD positioning during insertion, operator error, and inherent design features of the insertion device itself. The insertion devices of the present disclosure are configured to reduce resistance and friction during the IUD insertion process. The insertion devices are configurable to operate smoothly, quickly, steadily, easily, and in a highly controlled and consistent manner, thereby reducing trauma to the patient during insertion and deployment of the IUD.

The present disclosure provides insertion device structures and operation which controls the position of the IUD during various phases of the insertion procedure. Traditional insertion devices do not provide a reliable mechanism to position the IUD and maintain appropriate IUD positioning throughout the insertion procedure. Securing the IUD in the proper location during multiple stages of insertion is important for proper and painless insertion. Improper IUD positioning such as misalignment and premature or late deployment of the IUD can cause unsuccessful and painful insertion. The present disclosure provides improved position control through the use of position control features for control of both in-plane and longitudinal alignment of the IUD during the insertion procedure. In an aspect of the disclosed devices, the insertion device further includes position control feedback or signal features to provide verification and assurance of proper IUD positioning.

II. IUD Position & Alignment Control

The insertion devices of the present disclosure are configurable to exhibit a high degree of control and accuracy of the position of an IUD during an IUD insertion procedure using one hand. The insertion devices are configured to prevent the sheath slider from advancing distally beyond the distal cavity.

As will be appreciated by those skilled in the art, it is important to control the positioning and alignment of the IUD with a high degree of accuracy during the IUD insertion procedure. For example, in the IUD insertion procedure illustrated in FIGS. 3-5 and discussed above, it is important to control the longitudinal position of the IUD, in-plane alignment of the IUD, and cross-section of the t-shaped IUD 202 and insertion device sheath.

As discussed above, the t-shaped IUD 202 is rotatable r in-plane about longitudinal axis x as shown in FIG. 3D, such that the IUD arms or similar features of the IUD will deploy in-line with respective openings of the fallopian tubes 518*a*, 518*b* of the patient, as shown in FIG. 5B, to achieve an in-plane alignment. Generally speaking, when an IUD is in an in-plane alignment the IUD is laid flat, or substantially flat, within a plane defined by the openings of fallopian tubes 518*a*, 518*b* and cervical canal 521, such as the coronal plane shown x-y in FIG. 5B. The IUD arms 206*a*, 206*b*, or the like functional feature for a non-t-shaped IUDs, will be positioned near the openings of the fallopian tubes 518*a*, 518*b* when the IUD is deployed. The proximal end of the elongated body 204 of the t-shaped IUD is proximate to the internal orifice 523 of the cervix, and the IUD strings 210 extend proximally from the t-shaped IUD 202 into the vagina 524.

During phase 1 of the insertion procedure, as shown in FIGS. 4A-4B, the t-shaped IUD 202 is positioned within an insertion device 400 such that the t-shaped IUD 202 will not prematurely deploy but will deploy readily during the transition to phase 2 of the insertion procedure (FIG. 4C). The cross-section of a distal end 20 of the insertion device 400 is configurable such that it presents a minimal diameter along a longitudinal portion of the insertion device that is inserted into a patient's cervix and uterus, and the distal end 20 of the insertion device 400 is further configurable to present a distal end that is rounded or curved, smooth, and free of blunt or abrupt features. The use of a rounded distal tip which is free of blunt or abrupt features reduces or eliminates harm or trauma to the patient and reduces any impediment to smooth insertion of the insertion device through the cervical canal and into the uterus. The t-shaped IUD 202 is preferably deployed into the uterus having in-plane alignment such that the deployed IUD will be substantially in, for example, a coronal plane as discussed above.

III. IUDs and Hormones

A contraceptive device, which is available on the market and which releases levonorgestrel, consists of a t-shaped IUD 202 having an elongated body 204 fabricated of polyethylene equipped with a jacket-like polymeric reservoir 220 adjusted around the elongated body 204. The reservoir 220 contains an active agent. The active agent includes hormones used for the treatment of menopausal troubles or for contraception, such as levonorgestrel. The IUD is sold in sterile packaging together with the insertion device with the IUD positioned within a protective tube. The t-shaped IUD 202 is positioned at the forward end (distal end) with the hormone-containing elongate member protected by a sheath or tube. The IUD arms 206*a*, 206*b* of the transverse member, on the other hand, are expanded in order to prevent fatigue. The strings by which the t-shaped device is retracted towards the outside run between the plunger and the protective tube and end at the end of the handle.

IV. IUD Insertion Device

Figure 6A:
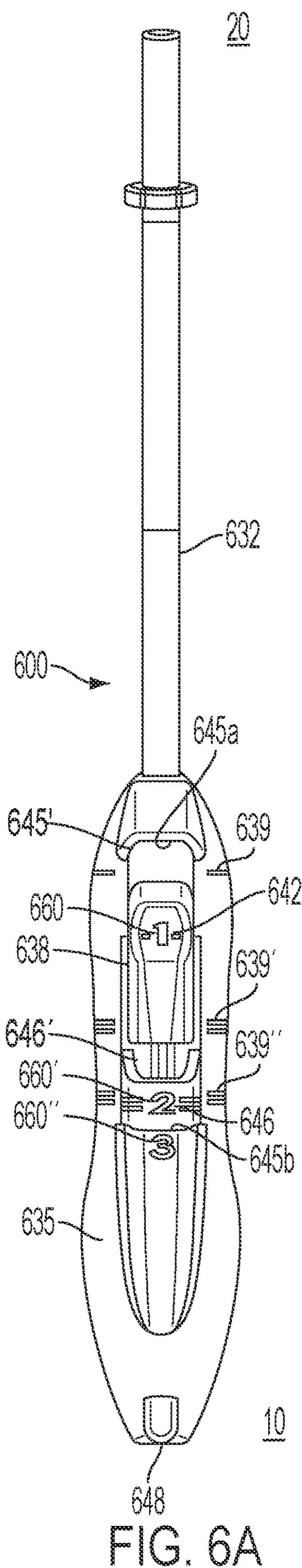
FIG. 6A illustrates a top view and FIG. 6B illustrates a side view of an insertion device with telescoping sliders.
Figure 6B:
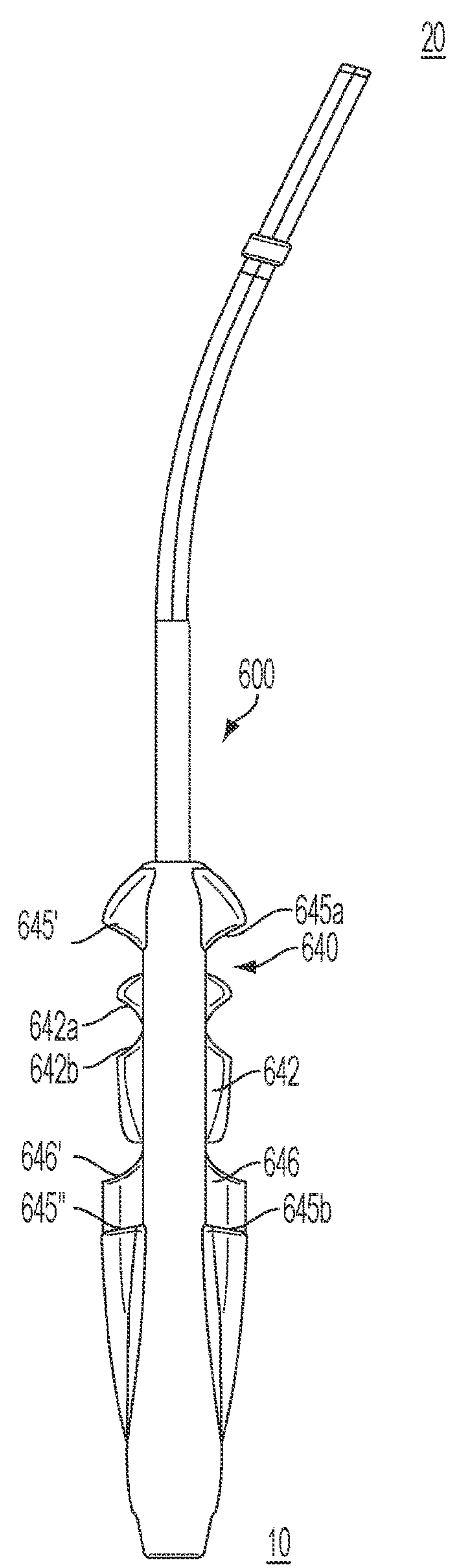
Figure 6C:
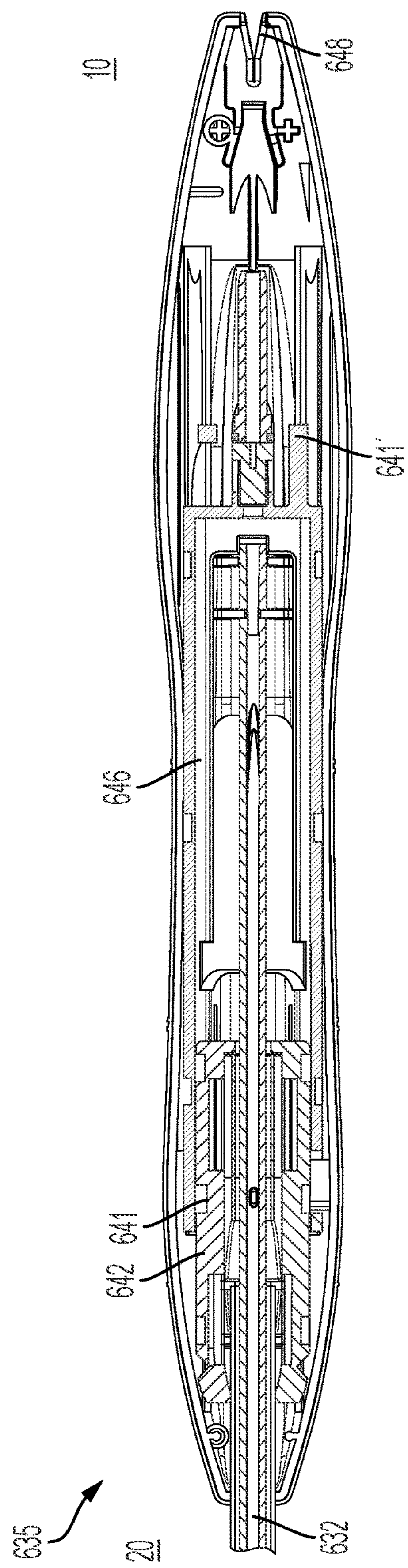
FIG. 6C illustrates a prior interior view of the handle of the insertion device.
Figure 6D:
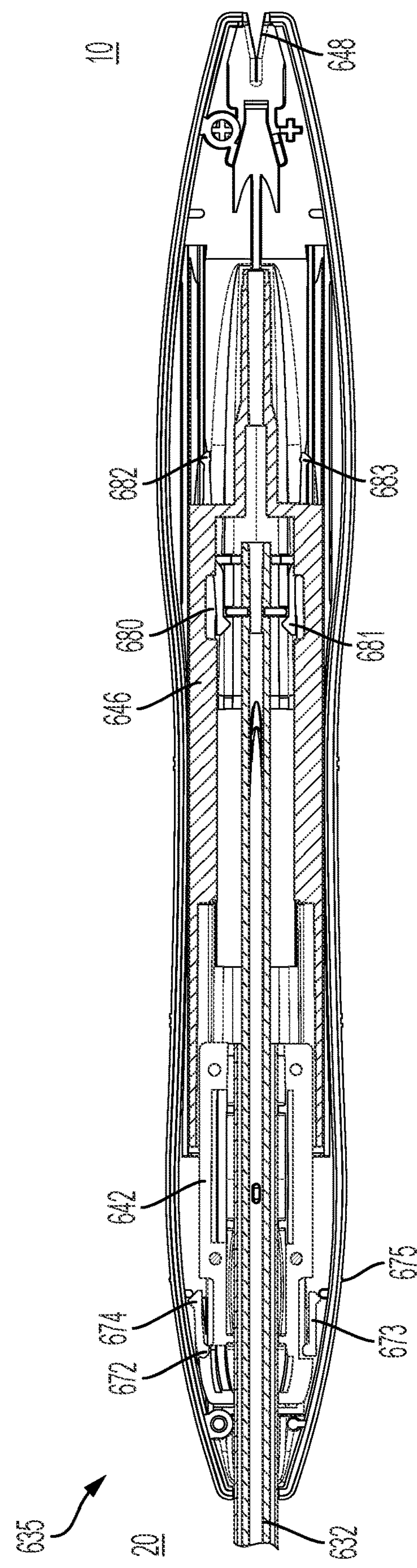
FIG. 6D illustrates an interior of an exemplar insertion device.
Figure 6E:
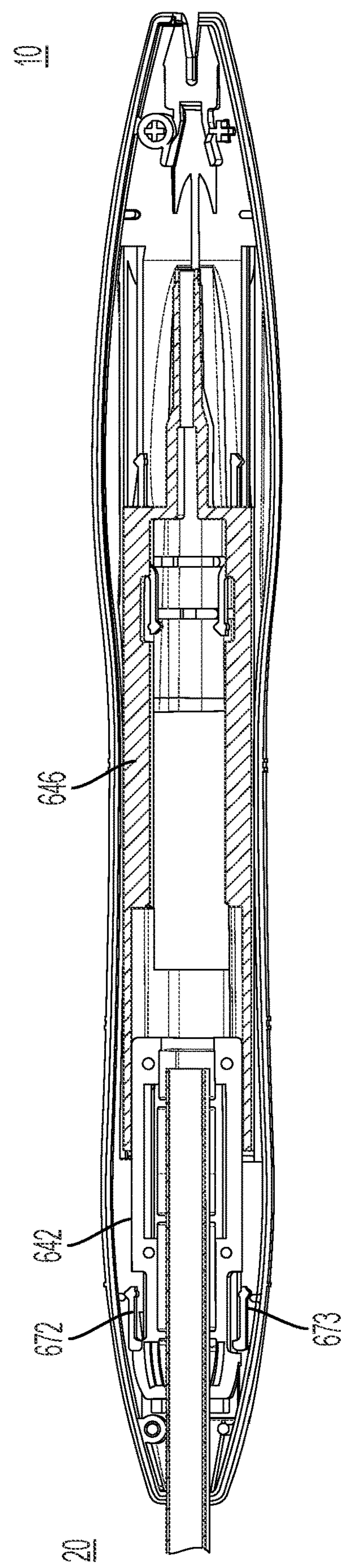
FIG. 6E illustrates an interior of an alternative exemplar insertion device.
Figure 6F:
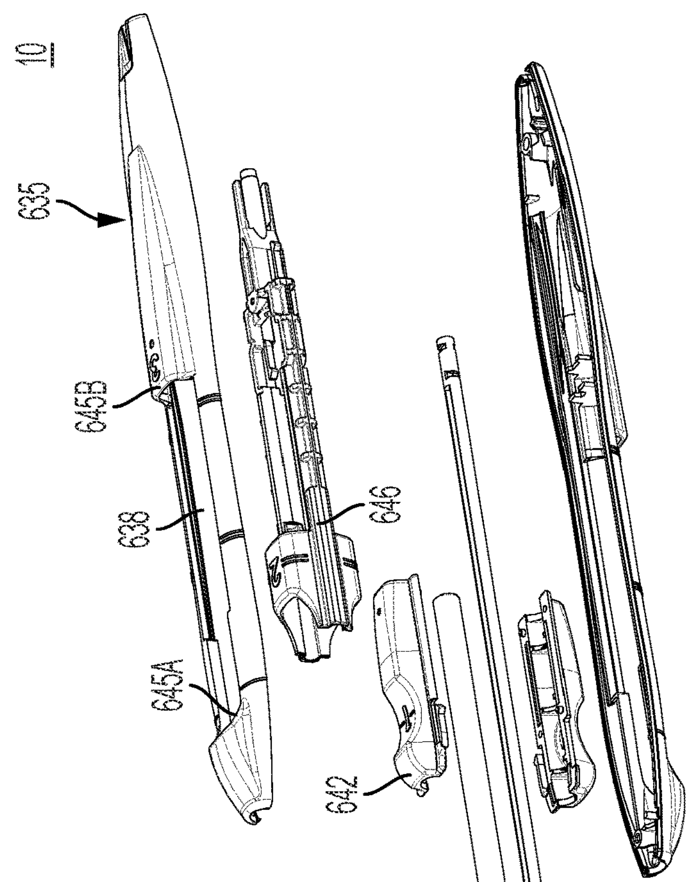
FIG. 6F is an exploded view of the insertion device of FIG. 6D.
Figure 6F:
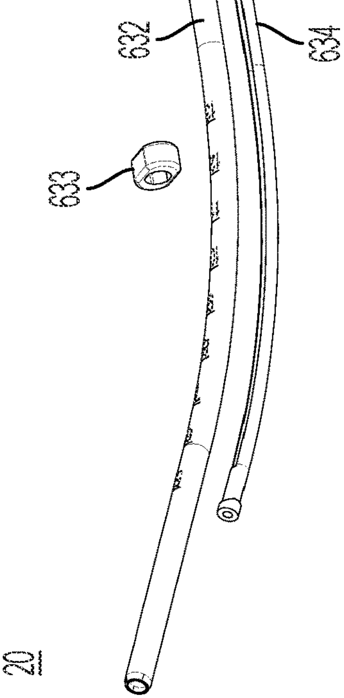
Figure 6G:
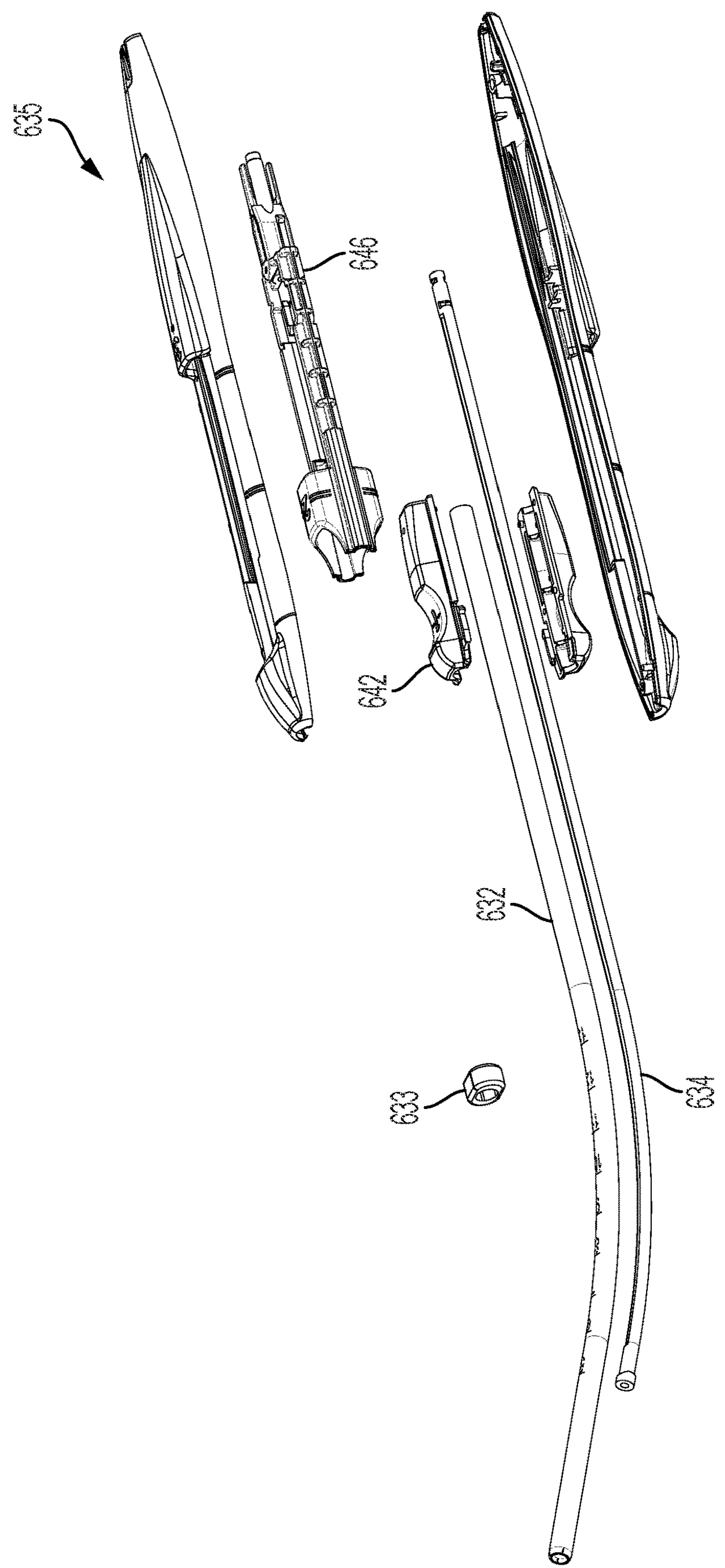
FIG. 6G is an exploded view of the insertion device of FIG. 6E.

FIGS. 6A-6E illustrate an insertion device 600. FIGS. 6A-6B are top and side views of the insertion device 600. FIG. 6C is a cross-sectional view of a prior version of the insertion device 600. FIG. 6D is a cross-section of an embodiment of the insertion device 600; FIG. 6E is a cross-section of an alternative embodiment of the insertion device 600. FIG. 6F is an exploded view of the insertion device 600 of FIG. 6A-B; FIG. 6G is an exploded view of the insertion device 600 of FIG. 6E.

The insertion device 600 comprises an elongated sheath 632 or tube having an interior lumen configured to house the IUD prior to deployment, an elongated inner member or plunger that fits within the elongated sheath 632, a handle 635 or housing, an elongated channel 638, a first slider that is a sheath slider 642 having a depression with a first sheath slider alignment surface 642A and a second sheath slider alignment surface 642B opposite the first sheath slider surface 642A, for controlling the translational movement of the elongated sheath 632 and the elongated inner member relative to one another along a corresponding longitudinal axis of the elongated channel 638, and a second slider which is a string control slider 646, having a first string control slider alignment surface 646A for controlling one or more strings attached to the IUD. The elongated channel 638 guides movement of the sheath slider 642 and the string control slider 646 in a proximal and distal direction along a longitudinal axis.

As explained in further detail below, the string control slider 646 can control the locking and unlocking of one or more strings attached to the IUD.

The handle 635 of the insertion device 600 is adaptable and configurable to provide a housing for insertion device parts such as the elongated sheath 632, plunger, and the sheath slider 642 and the string control slider 646, and provides a handle for the operator to hold the insertion device 600 during operation.

The handle 635 can have a marking 639, such as a single raised line, related to a step in the insertion procedure, e.g., "1" corresponding to phase 1 of the procedure with a corresponding marking on the sheath slider 642. The string control slider 646 and the handle 635 can have a marking 639', such as two raised lines, related to a step in the insertion procedure, e.g. "2." The handle 635 can have another marking 639", also two raised lines related to a step in the insertion procedure, e.g., "3."

The handle 635 is further adaptable and configurable to include an elongated channel 638 which allows user access to the sheath slider 642 and the string control slider 646. As will be appreciated by those skilled in the art, movement of the sliders along the length of the elongated channel 638 can be one or more of concurrent or independent, at any given time during the procedure.

As illustrated, the sheath slider 642 is a sheath slider which is attachable to elongated sheath 632 and directly controls the longitudinal location and translational movement of the elongated sheath 632 relative to the elongated inner member and IUD as it moved within the elongated channel 638. The string control slider 646 unlocks or releases the strings of the IUD. During an insertion procedure, the operator's thumb is used to move both the sheath slider 642 and the string control slider 646 in a proximal direction (i.e., towards the proximal end 10) and a distal direction (i.e., towards a distal end 20) along the elongated channel 638 to control the elongated sheath 632 and IUD strings, respectively. As will be appreciated by those skilled in the art, during routine insertion, the user would only need to move the sliders in the proximal direction. Only if there were a need to reload the IUD would the user move in the distal direction.

The sheath slider 642 and the string control slider 646 each have alignment surfaces and move within the elongated channel 638 along a longitudinal axis in a proximal direction or a distal direction. At the distal end 20 of the elongated channel 638 is a cavity 645 having a cavity alignment surface 645' within the handle 635 into which at least a portion of the distal end of the sheath slider 642 can be advanced. Interior features of the handle 635 and the sheath slider 642 prevent the sheath slider 642 from advancing distally to a point where the distal surface of the finger indent 660 is flush with an edge of the first cavity 645*a*. The second cavity 645B has a cavity alignment surface 645" that aligns with the string control slider alignment surface 646' when the string control slider 646 is in a rearward (proximal) position. The second sheath slider alignment surface 642B aligns with the string control slider alignment surface 646' when the string control slider 646 is in a first rearward (proximal) position, and both the string control slider alignment surface 646' and the cavity alignment surface 645" when both the sheath slider 642 and the string control slider 646 are in a is second rearward (proximal) position.

The sheath slider 642 and the string control slider 646 have a telescopic configuration, whereby at least one slider slides within or through at least a portion of one other slider along the longitudinal axis. As shown in FIGS. 6A-B for example, the sheath slider 642 can slide under a portion of the string control slider 646.

The first cavity 645*a* is positioned at a first end of the elongated channel 638 and the second cavity 645B is positioned at a second end of the elongated channel 638. The second cavity 645B has a cavity alignment surface 645" that aligns with the first sheath slider alignment surface 642A when the first sheath slide is in a rearward position. During phase 3 of the insertion procedure, the sheath slider 642 and string control slider 646 are in the full proximal position along the longitudinal axis of the elongated channel 638, and at least partially surrounded by the second cavity 645B.

Additional visual indication features and/or tactile features can be provided. Visual indication features can be provided on the elongated sheath 632, the handle 635, or both. The proximal end of the handle has a string control surface 648. The string control surface 648 also provides a visual indicator for the user that the strings of the IUD have been released during the insertion process. As noted above, the numbers 1, 2, and 3 on the insertion device components provide a visual indication to the user the appropriate positions of the insertion device components during the multiple phases of the insertion procedure. Visual indicators, such as numbers, can be applied in any suitable fashion including, but not limited to, printing, etching, molding, carving, and the like. Moreover, visual indicators can be positioned such that they are visible only during certain aspects of the procedure, and not visible during other aspects of the procedure. Additionally, the visual indicators can be both visible and tactile.

As shown in FIG. 6C, an interior of a prior version of the insertion device 600 included detent ribs 641, 641' of the string control slider 646 that flexed within the plane of the ultrasonic weld of the handle halves. The detent ribs 641, 641' within the plane of the ultrasonic weld of the handle 635 halves led to detent force variability.

As shown in FIG. 6D, the distally positioned sheath slider detent arms 672, 673 have been reconfigured so that the distally positioned sheath slider detent arms 672, 673 flex 90 degrees relative to the ultrasonic weld plane of the handle halves. In one configuration, the sheath slider 642 has distally positioned sheath slider detent arms 672, 673 on either side of both the top and bottom halves of the sheath slider 642, as shown in more detail in FIG. 7A.

FIG. 6E, is an alternative configuration, where each half of the sheath slider 642 has one detent arm. When the two halves of the sheath slider 642 are mated, a detent arm is positioned on each side of the sheath slider 642, as shown in more detail in FIG. 7B. The distally positioned sheath slider detent arms 672, 673 are positioned on either side of the sheath slider 642 when the two pieces of the sheath slider are assembly. The distally positioned sheath slider detent arms 672, 673 can be positioned on both sides of each half of the sheath slider 642, on both sides of one half of the sheath slider 642, or on opposing sides of each half of the sheath slider 642.

FIG. 6F is an exploded view of the insertion device 600 of FIG. 6D. FIG. 6G is an exploded view of the insertion device 600 of FIG. 6E. The insertion device 600 includes a handle 635, shown in two pieces. The handle has an elongated channel 638 or guide and a distal cavity or first cavity 645A and a proximal cavity or second cavity 645B which faces the first cavity 645A at an opposite side of the elongated channel 638. A sheath slider 642 is positioned distally relative to a string control slider 646. An elongated sheath 632, a plunger 634 and a flange 633 is provided.

Figure 7A:
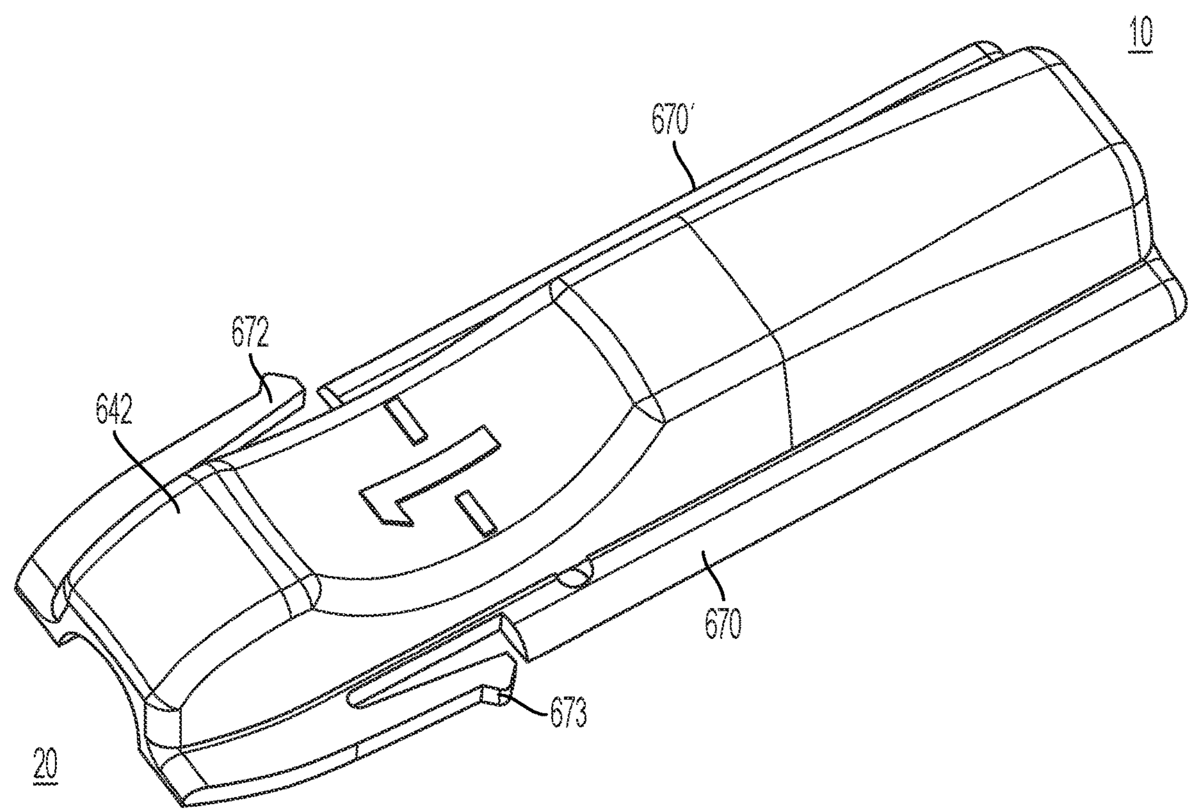
FIGS. 7A-D, 8, 9, 10, 11, 12A-E, 13A-C, 14, 15 and 16 are detailed views of components of the insertion device shown in FIGS. 6A-E.

FIG. 7A illustrates additional detail of the sheath slider 642 shown in FIG. 6E. The top half of the sheath slider 642 has a pair of lateral rails 670, 670' on either side of the sheath slider 642. The lateral rails 670, 670' fit within a channel on either side of the housing (shown in FIG. 9). A pair of distally positioned sheath slider detent arms 672, 673 are provided distal to the lateral rails 670. The distally positioned sheath slider detent arm 672*s* 672, 673 are lateral flexing detent arms.

Figure 7B:
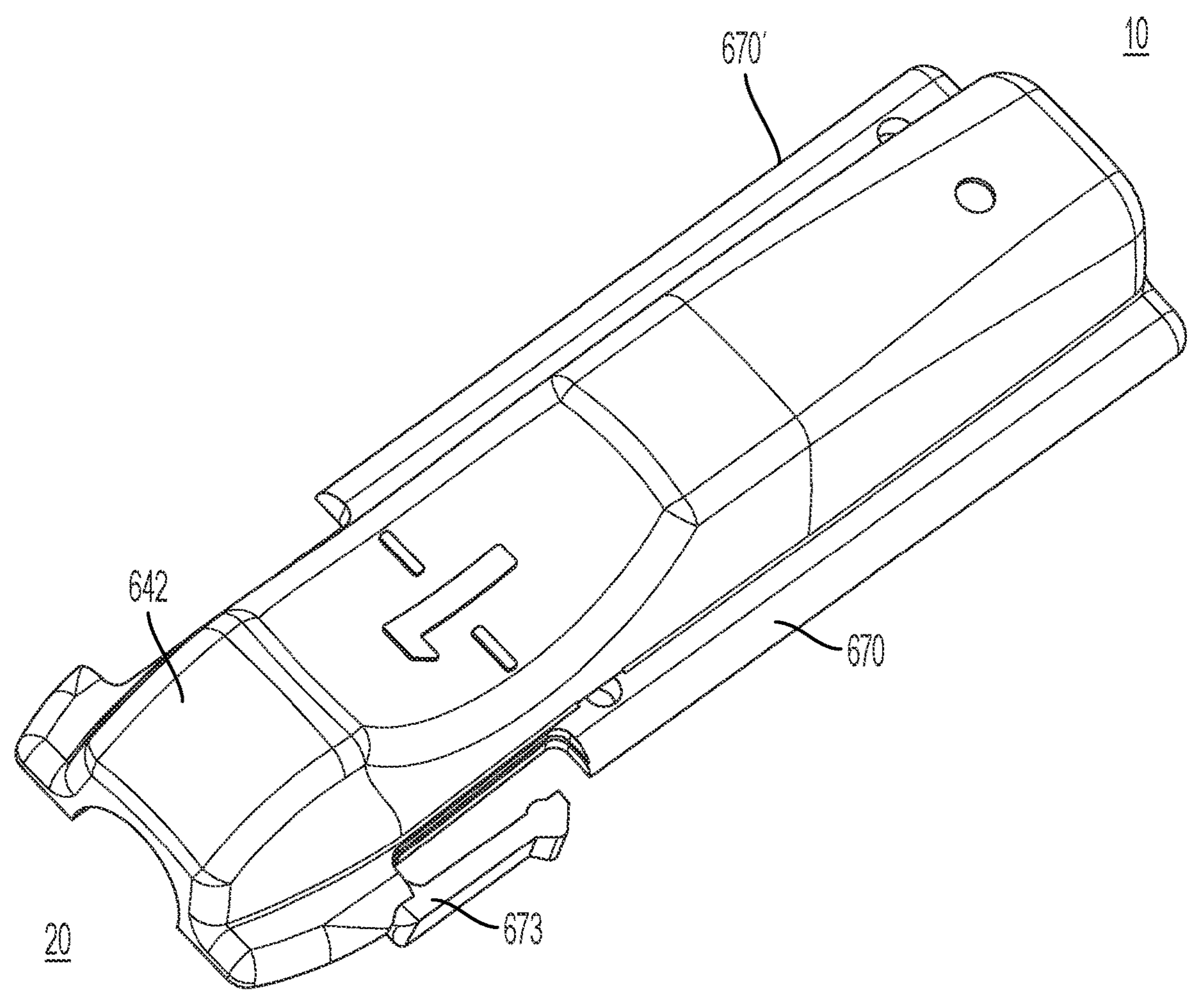

FIG. 7B illustrates additional detail of the sheath slider 642 shown in FIG. 6E. The top half of the sheath slider 642 has a pair of lateral rails 670, 670' on either side of the sheath slider 642. The pair of lateral rails 670, 670' fit within a channel in the housing (shown in FIG. 9). A distally positioned sheath slider detent arm 673 is provided distal to the lateral rails 670. The distally positioned sheath slider detent arm 673 is a lateral flexing detent arm. In one configuration, the bottom half of the sheath slider 642 could have a distally positioned sheath slider detent arm on a side opposite the distally positioned sheath slider detent arm 673 so that when the top and bottom of the sheath slider 642 are mated, a sheath slider detent arms extend from either side of the sheath slider 642.

Figure 7C:
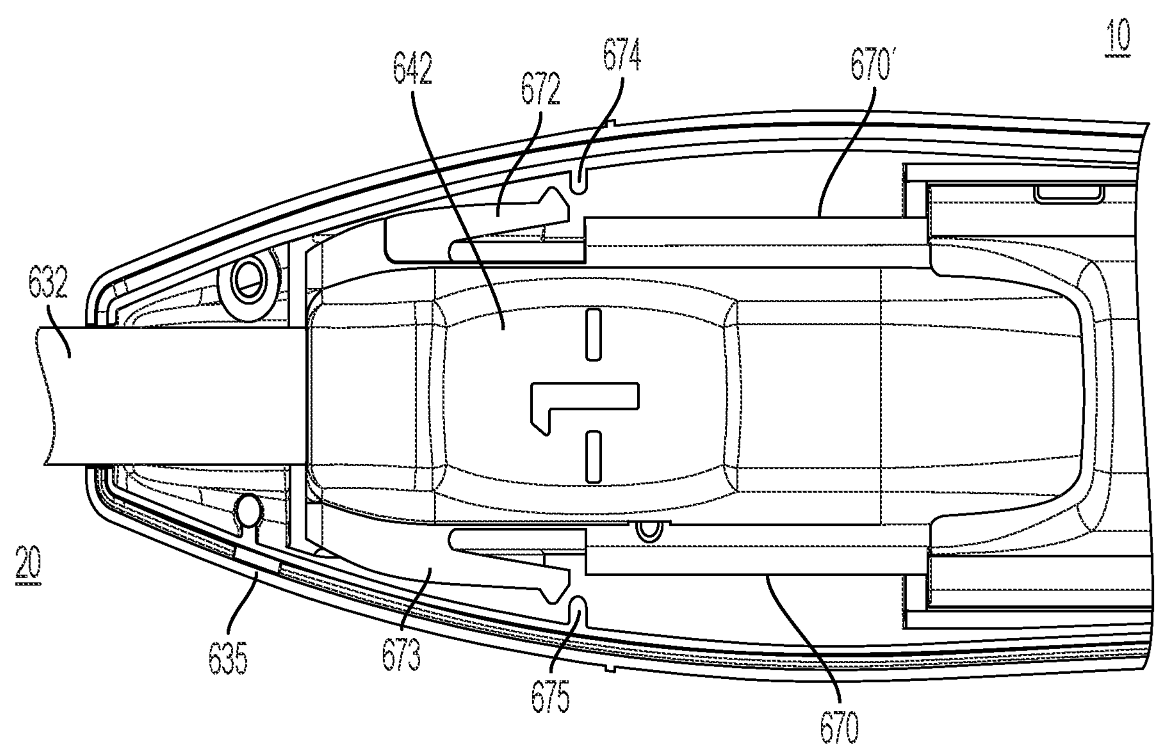

FIG. 7C illustrates the sheath slider 642 shown in FIG. 7A positioned within a portion of the housing for the handle 635. A pair of lateral ribs 674, 675 which extend from an interior surface of the housing of the handle 635 engage the distally positioned sheath slider detent arms 672, 673. The sheath slider 642 engages the elongated sheath 632 at a distal end 20, and a string control slider 646 at a proximal end 10. The sheath slider 642 has a visual indicator, such as a "1" on a concave upper surface. The concave upper surface is designed to fit a finger of a user during one-handed use of the IUD insertion device.

Figure 7D:
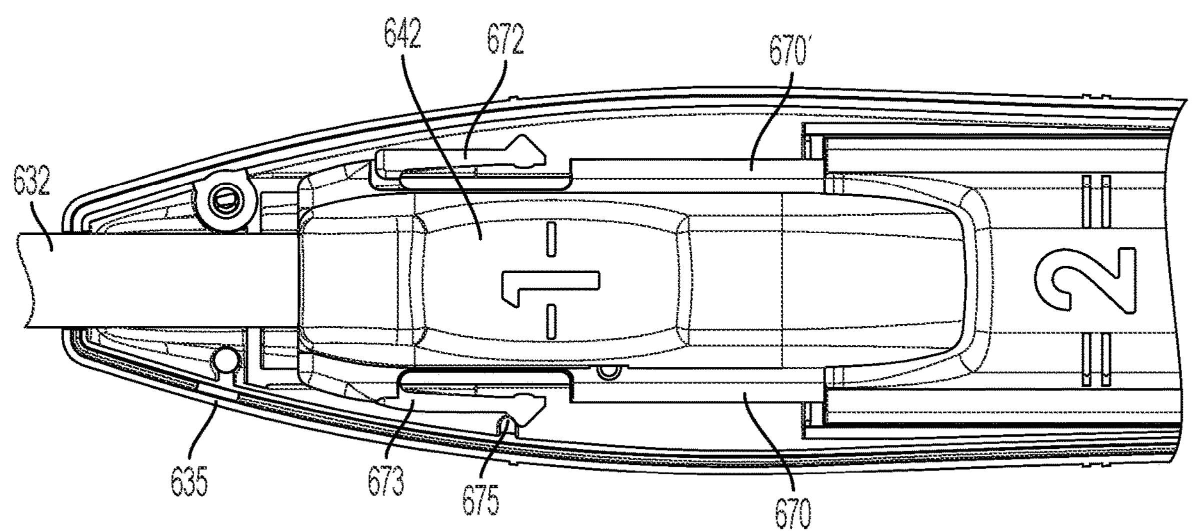

FIG. 7D illustrates the sheath slider 642 shown in FIG. 7B positioned within a portion of the housing of the handle 635. A lateral rib 675 extends from an interior surface of bottom half of the housing of the handle 635 to engage a proximal surface of the lateral rib 675. The sheath slider 642 engages the elongated sheath 632 at a distal end 20. and a string control slider 646 at a proximal end 10.

Figure 8:
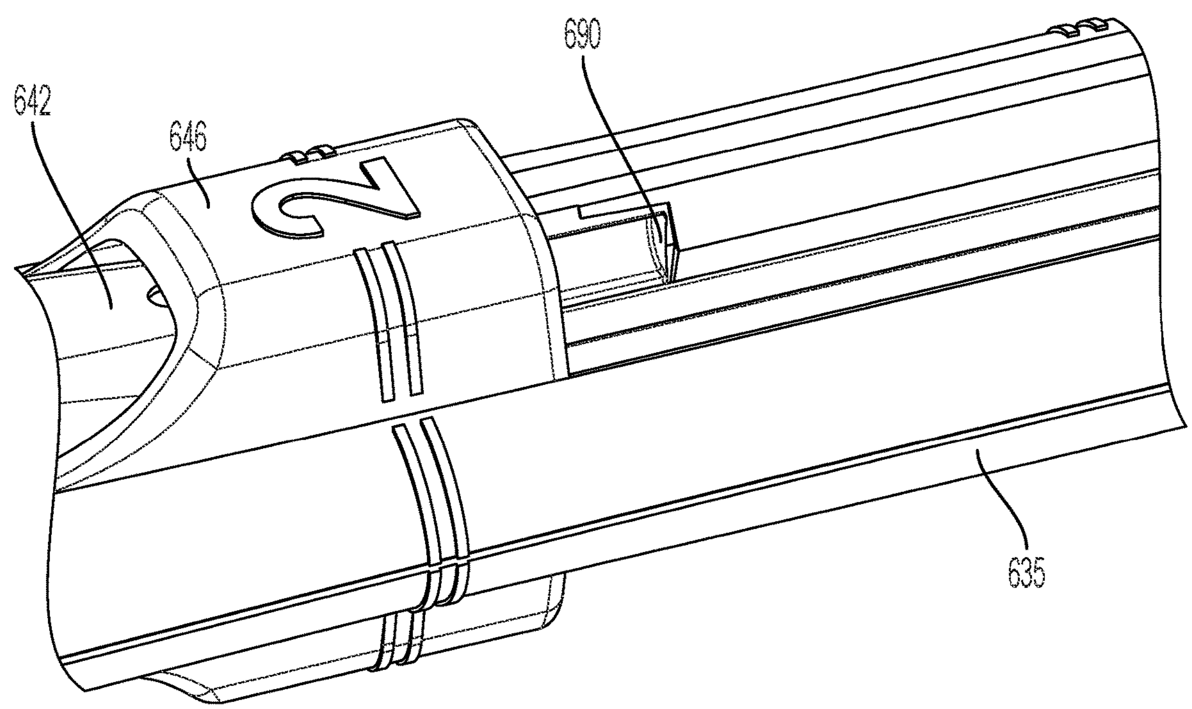

FIG. 8 illustrates the sheath slider 642 positioned partially within a cavity formed in the string control slider 646 with a first sheath hard stop surface 690 on an interior surface of the string control slider 646. The first sheath hard stop surface 690 prevents the sheath slider 642 from moving proximally past the string control slider 646 during use.

Figure 9:
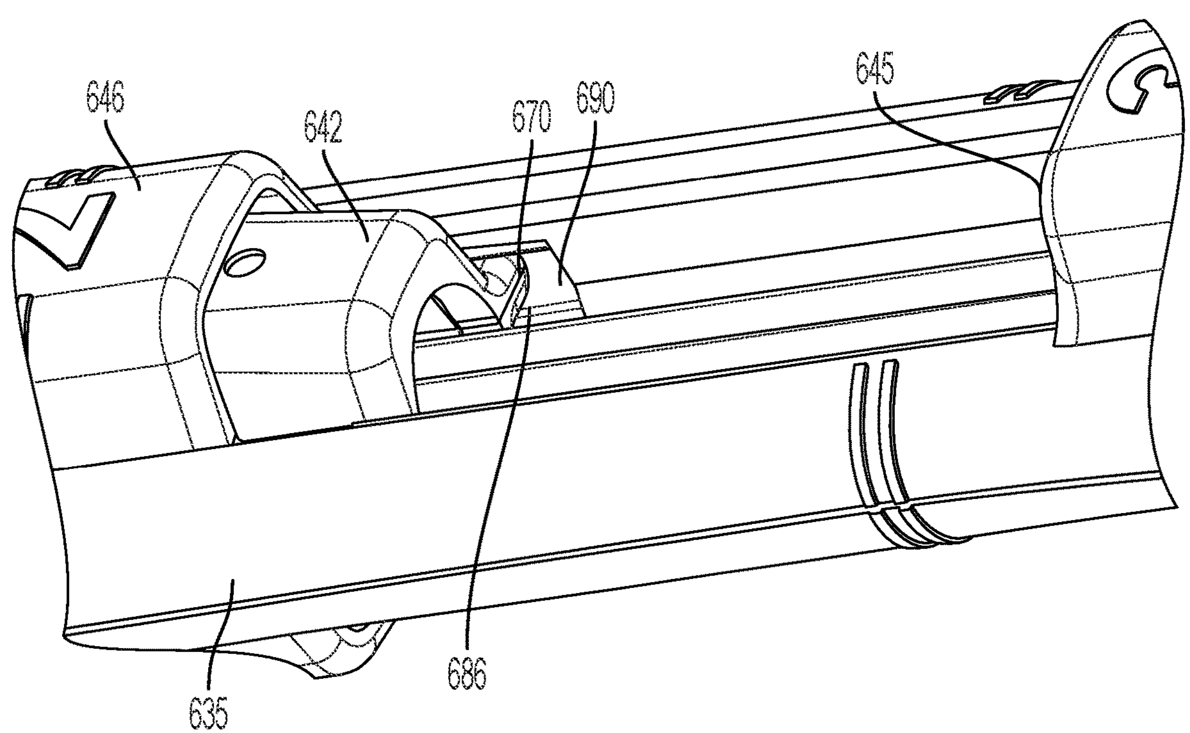

FIG. 9 illustrates another view of the sheath slider 642 positioned partially nested within a cavity formed in the string control slider 646 with a first sheath hard stop surface 690 on an interior surface of the string control slider 646. The channel 686 that the one of the lateral rails 670 fits within can be appreciated from this view.

Figure 10:
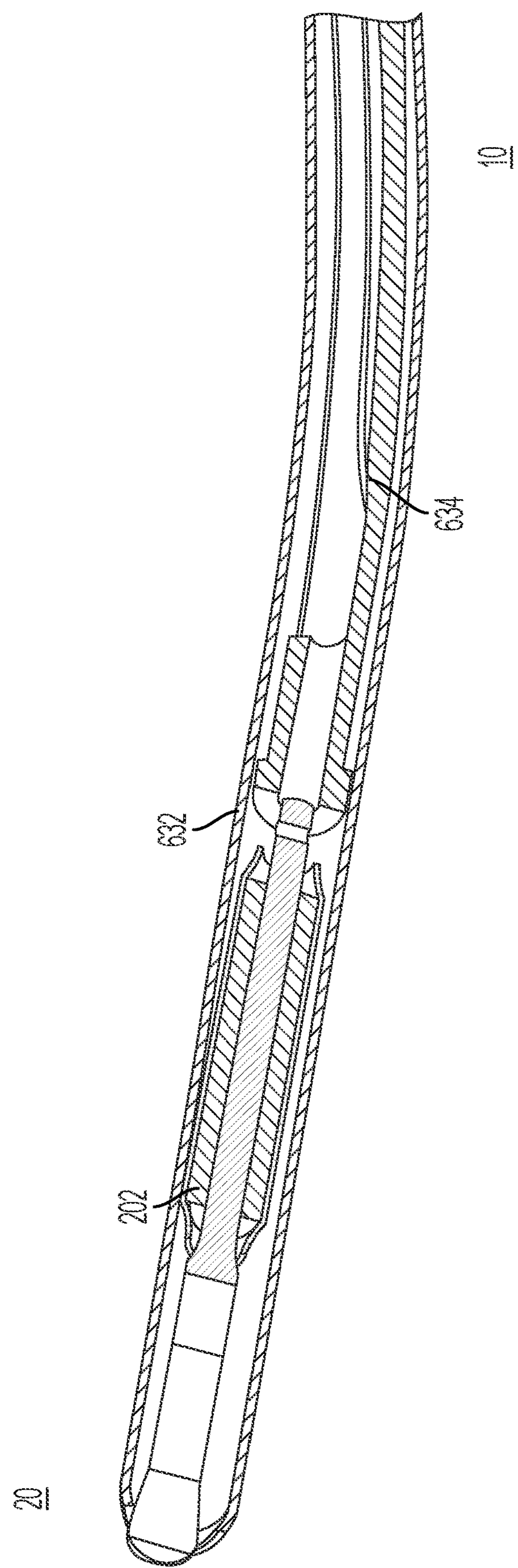

FIG. 10 illustrates a distal end 20 of the insertion device 600 of FIG. 6A. The t-shaped IUD 202 is positioned in the distal end 20 of the elongated sheath 632. The plunger 634 engages the proximal end 10 of the t-shaped IUD 202 without the use of any additional tube segment.

Figure 11:
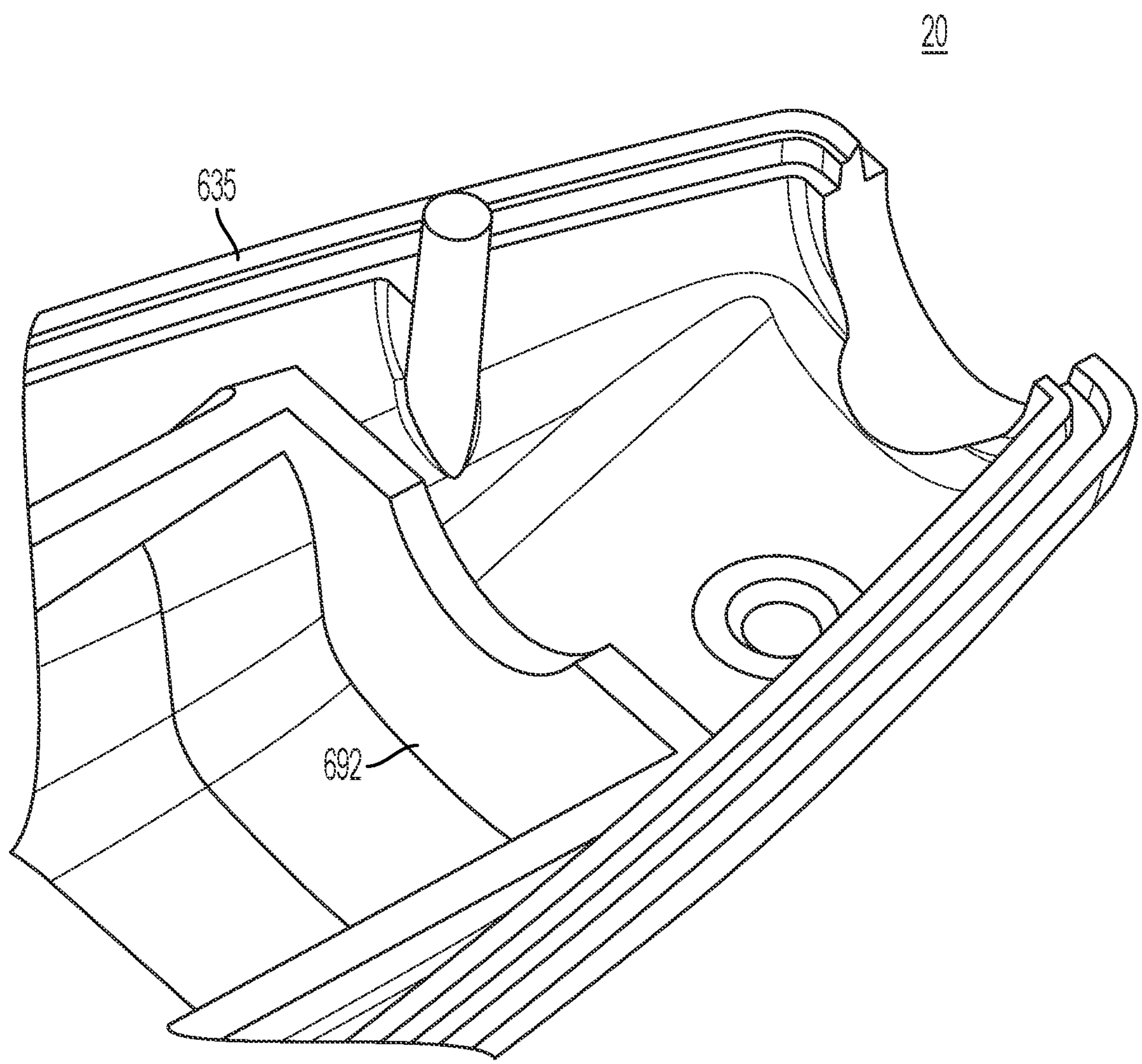

FIG. 11 illustrates an interior view of a distal portion of the handle 635 adjacent the elongated sheath 632 shown in FIG. 6C. An elongated sheath hard stop surface 692 is provided which eliminates the need to provide an inner sleeve inside the elongated sheath 632 to prevent further movement of the elongated sheath 632.

Figure 12A:
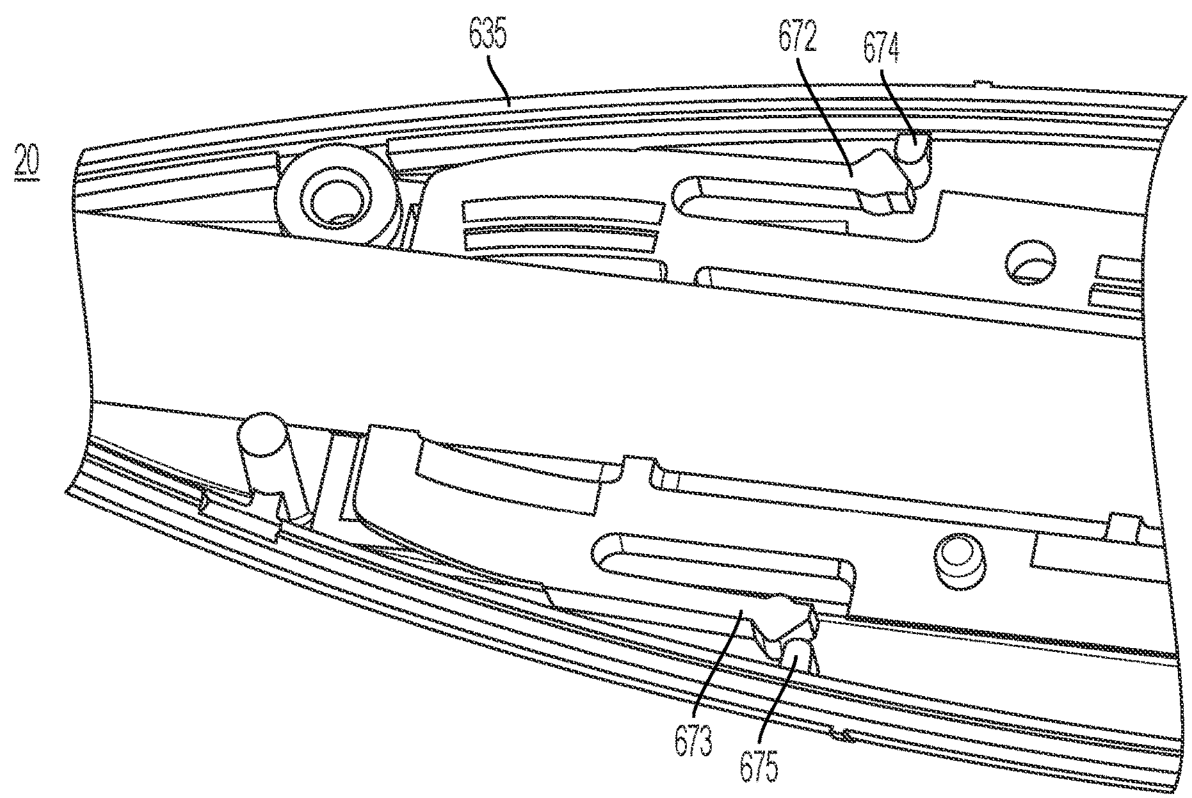
Figure 12B:
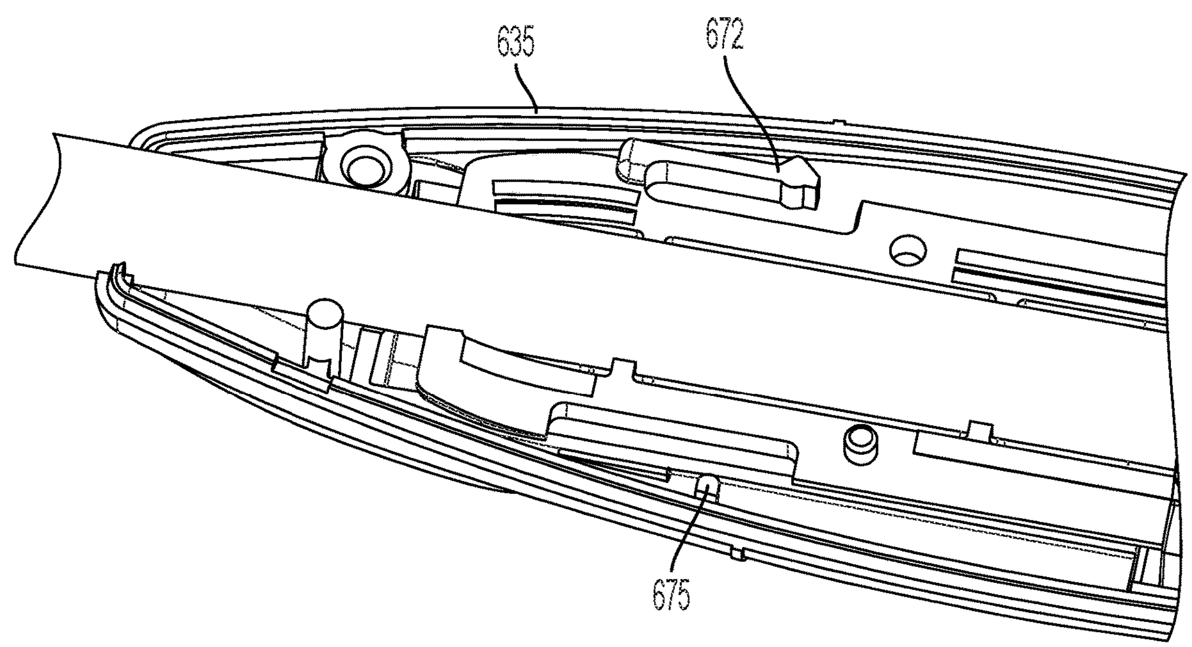
Figure 12C:
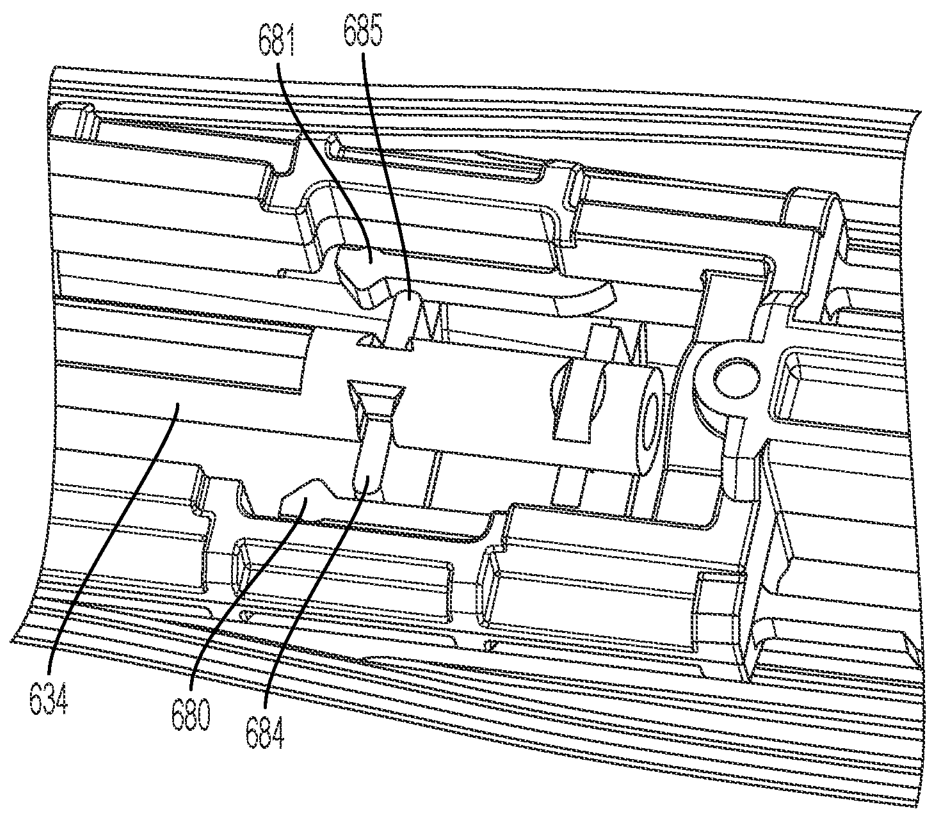

FIGS. 12A-12C illustrate elements of the insertion device 600 during various steps of the insertion process. FIG. 12A illustrates an interior of the insertion device in position 1 at the beginning of the insertion procedure (phase 1) when the sheath slider 642 of FIG. 6A is in a distal position. As shown in the cut-away, the distally positioned sheath slider detent arms 672, 673 engage the lateral ribs 674, 675 on the bottom half of the handle 635.

FIG. 12B illustrates position 1 of an alternate embodiment at the beginning of the insertion procedure (phase 1) when the sheath slider 642 is in a distal position. As shown in the cut-away, one of the distally positioned sheath slider detent arms 672 is positioned on the lower portion of the sheath slider 642 and would engage a lateral rib positioned within the upper half of the handle (not shown). A lateral rib 675 is shown on the opposing side of the bottom half of the handle 635, which would engage a lateral rib positioned within the upper portion of the sheath slider.

FIG. 12C illustrates an interior of the insertion device in position 2 midway during the procedure (phase 2). Interiorly engaging string control slider detent arms 680, 681 are positioned proximal to the distally positioned sheath slider detent arms 672, 673. The interiorly engaging string control slider detent arms 680, 681 engage a pair of ribs 684, 685 which engage the plunger 634 on one side and the interiorly engage string control slider detent arms 680, 681 on the other side. The interiorly engaging string control slider detent arms 680, 681 of position 2 (phase 2) provide the user tactile feedback that they have reached the second position. When this feedback occurs, the user then waits 15 seconds for the IUD arms to come down. Then the user moves the sheath slider 642 together with the string control slider 646 out of position 2 and proximally into position 3.

Figure 12D:
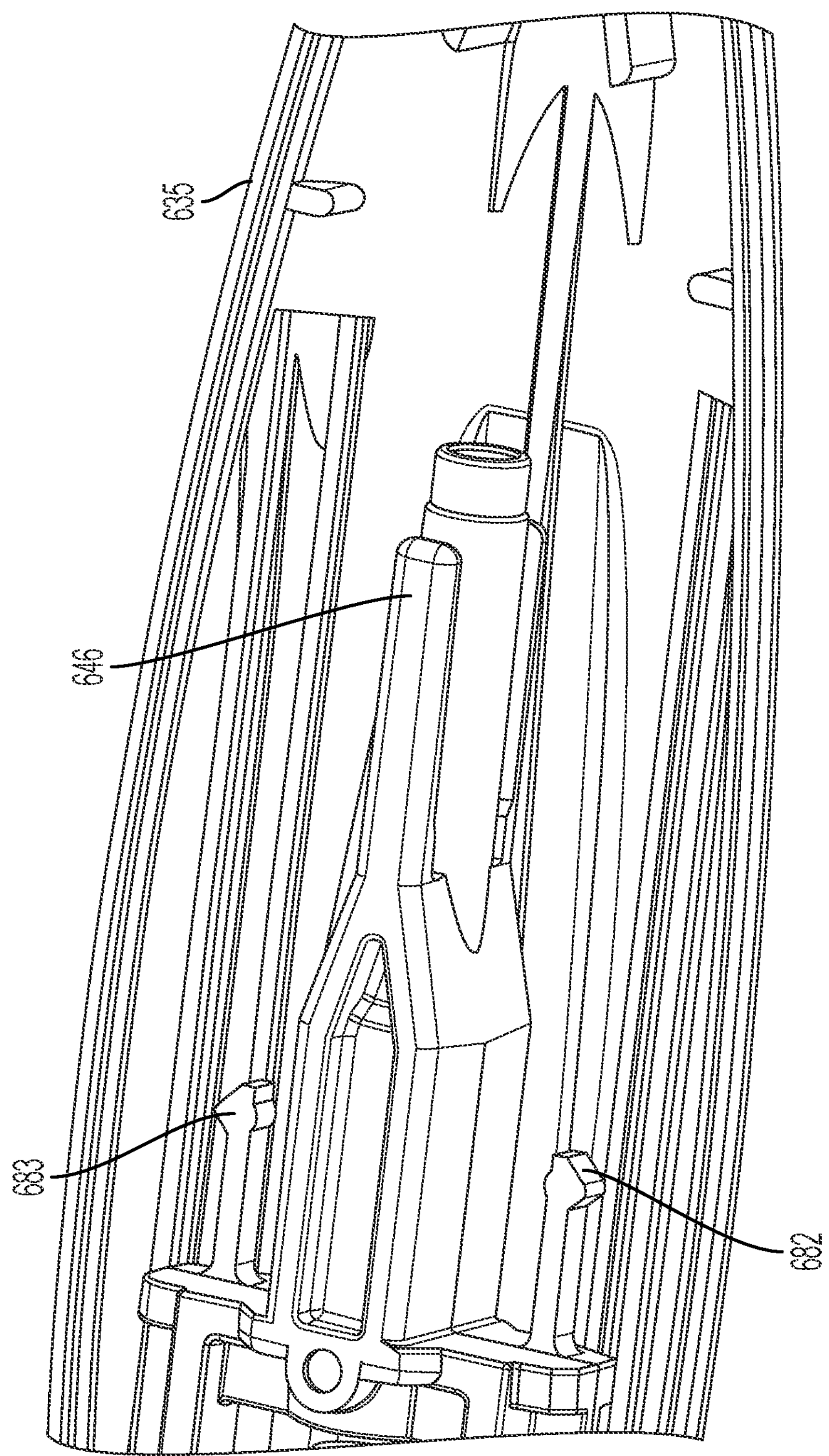
Figure 12E:
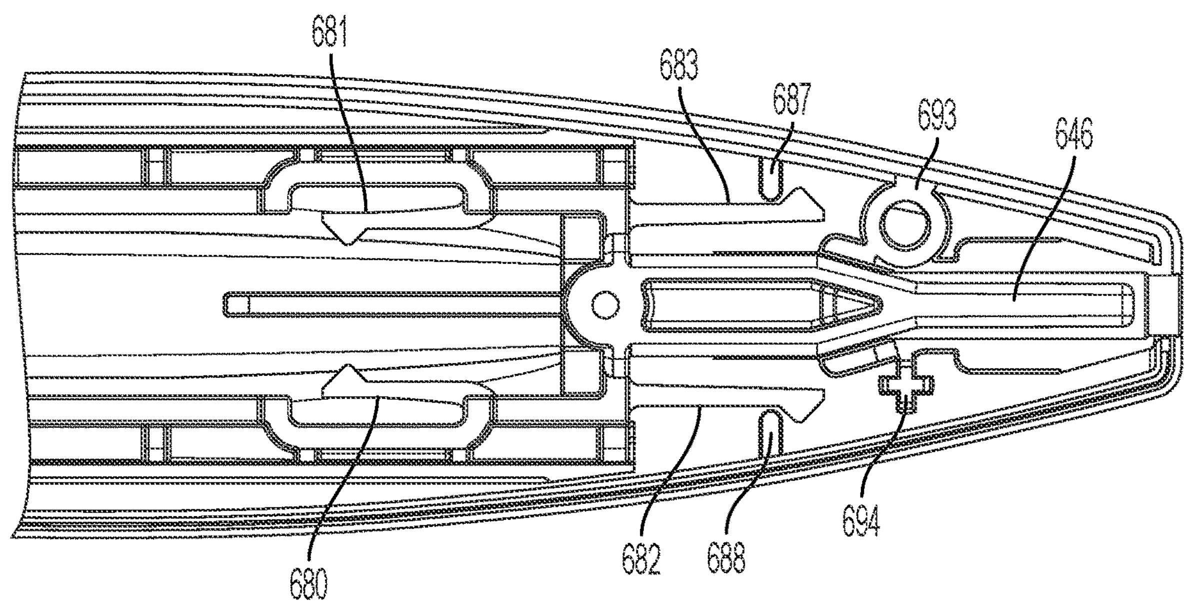

FIG. 12D a proximal end 10 of the interior of the handle 635 during position 3 showing the proximal end of the string control slider 646. A pair of outwardly facing string control slider detent arms 682, 683. The outwardly facing string control slider detent arms 682, 683 at position 3 again provide the user tactile feedback and an audible click to let the user know that position 3 has been reached. FIG. 12D illustrates the string control slider at position 3 with the outwardly facing string control slider detent arms 682, 683 engaging the proximal handle ribs 687, 688. Additional locating features 693, 694 shown in FIG. 12E are provided which assist in achieving proper alignment and quick positioning of the two handles prior to ultrasonic welding. The locating features are illustrated as an "O" and a "+" to distinguish a first locating feature on a first side of the handle 635 and a second locating feature on a second side of the handle 635 opposite the first side of the handle.

Figure 13A:
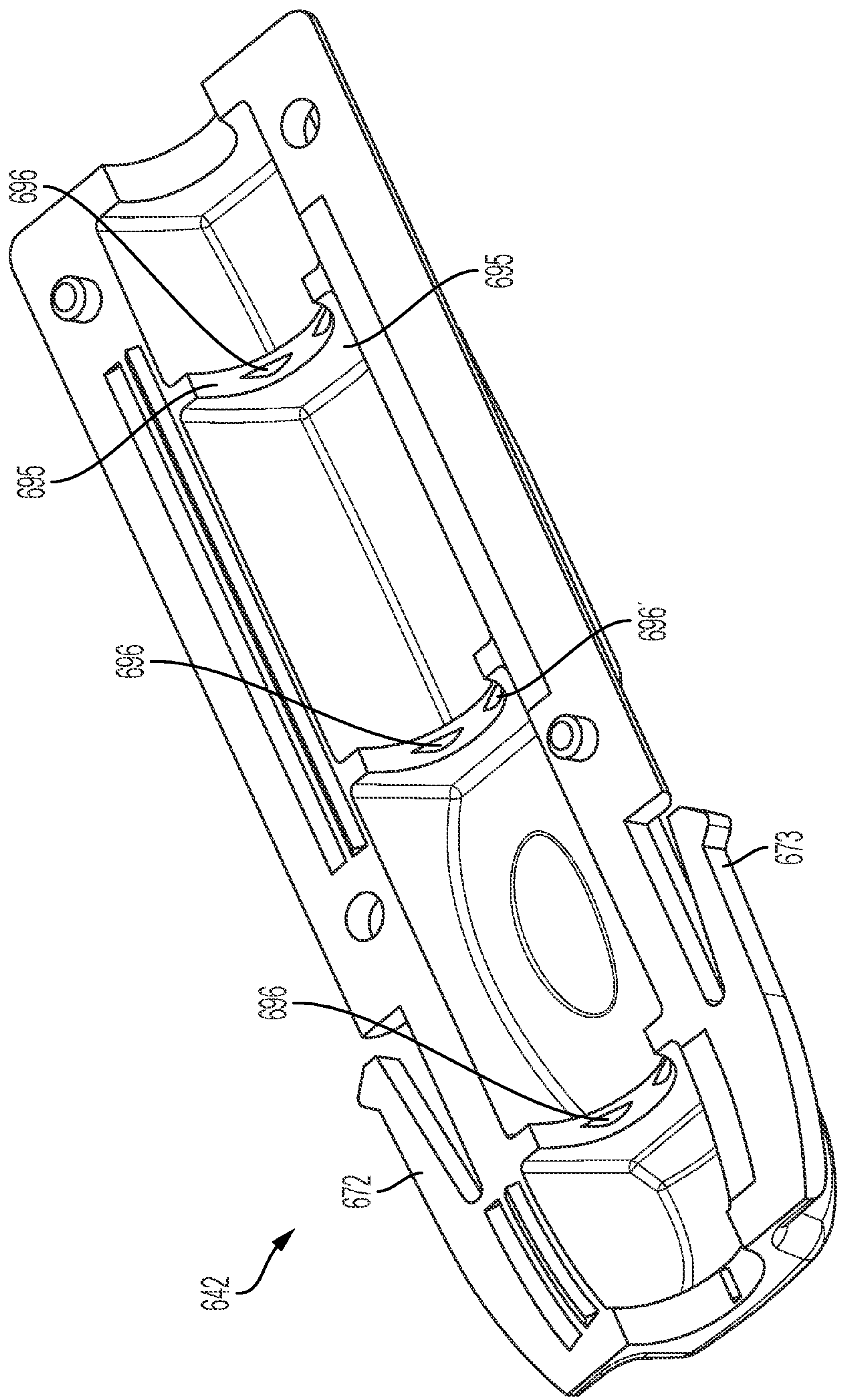
Figure 13B:
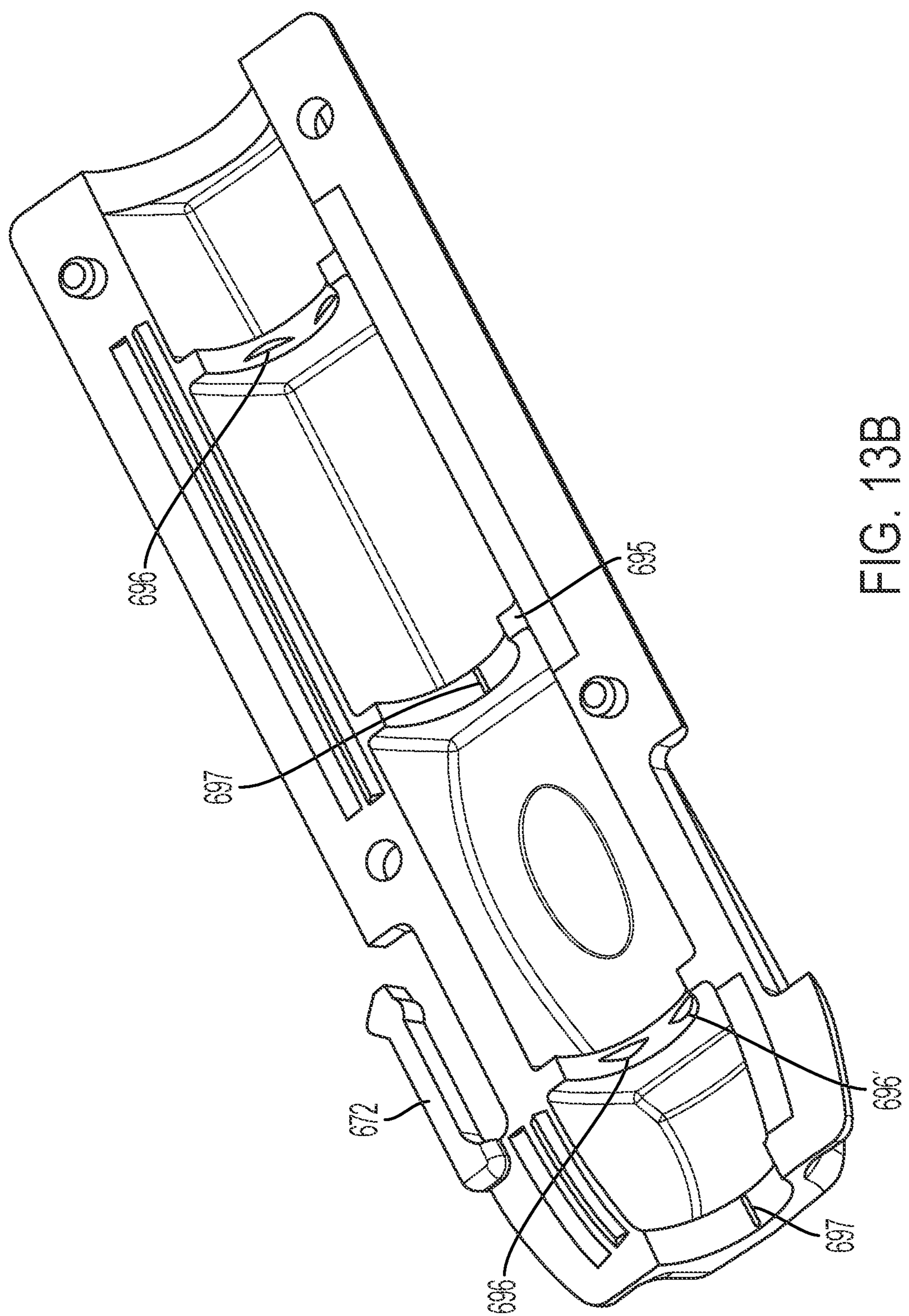
Figure 13C:
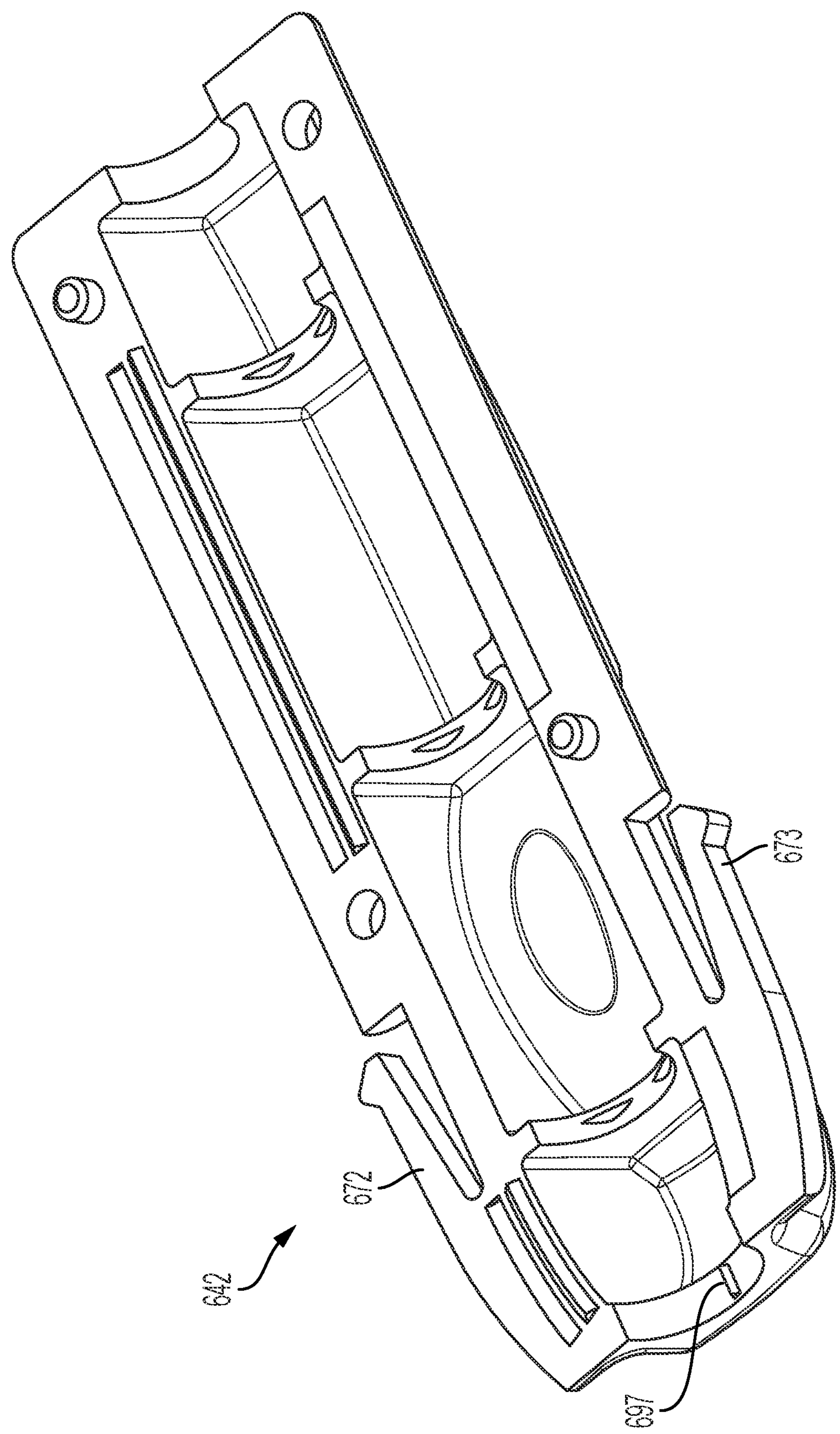

Turning to FIGS. 13A-C, the bottom half of the sheath slider 642 illustrating an interior surface has a plurality of internal curved ribs 695 (illustrated as three ribs) with a pair of tensile holders 696, 696' on an upper surface of one or more of the internal curved ribs 695. The pair of tensile holders 696, 696' provide additional tensile holding strength for the sheath slider 642 during use. Thus, in FIG. 13A, there are three internal curved ribs 695 wherein each of the three internal curved ribs each have two tensile holders, for a total of six tensile holders. FIG. 13B illustrates the use of alternating the tensile holders 696 and torsional holder 697 at a 90 degree angle from the tensile holder which provides additional torsional strength during use. Thus, in FIG. 13B, there are also three internal curved ribs 695. In this configuration, two of the internal curved ribs have two tensile holders, for a total of four tensile holders, and the third rib (the center rib) has a torsional holder 697.

The bottom half of the sheath slider 642 in FIG. 13A has a pair of distally positioned sheath slider detent arms 672, 673. The configuration illustrated in FIG. 13B shows the bottom portion of the sheath slider 642 with only one of the distally positioned sheath slider detent arms 672. As will be appreciated by those skilled in the art, the configuration of FIG. 13A having two of the distally positioned sheath slider detent arms 672, 673 can have a single detent arm and/or can have tensile holders 696 on one or more of the internal curved ribs 695 or can have a combination of tensile holders 696 and torsional holder 697. Similarly, the configuration shown in FIG. 13B can have two detent arms. FIG. 13C illustrates a bottom portion and interior surface of a sheath slider 642 with a torsional holder 697 at a front curved surface.

Figure 14:
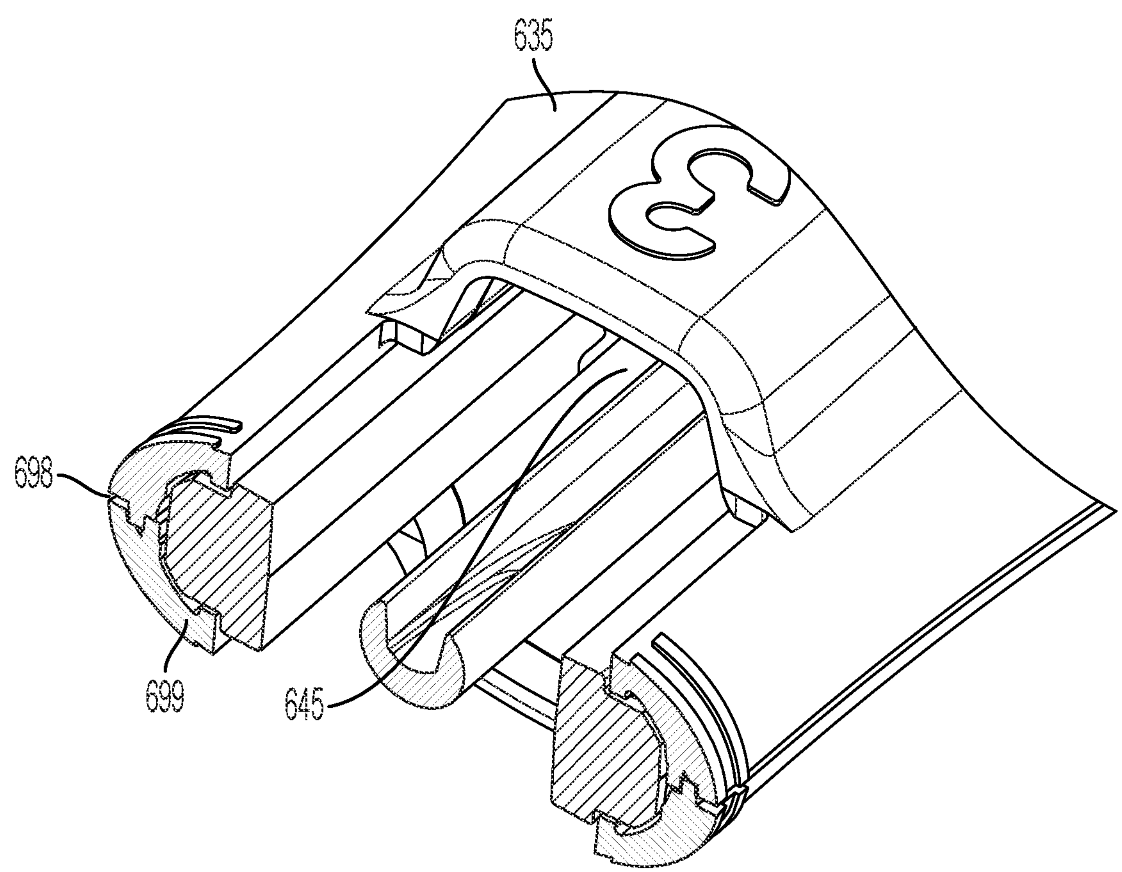

FIG. 14 illustrates a cut away of the housing forming the handle 635. A tongue and groove interface 698 is provided to improve the weld strength of the handle. Additionally rails 699 can be provided to increase rigidity of the handle 635.

Figure 15:
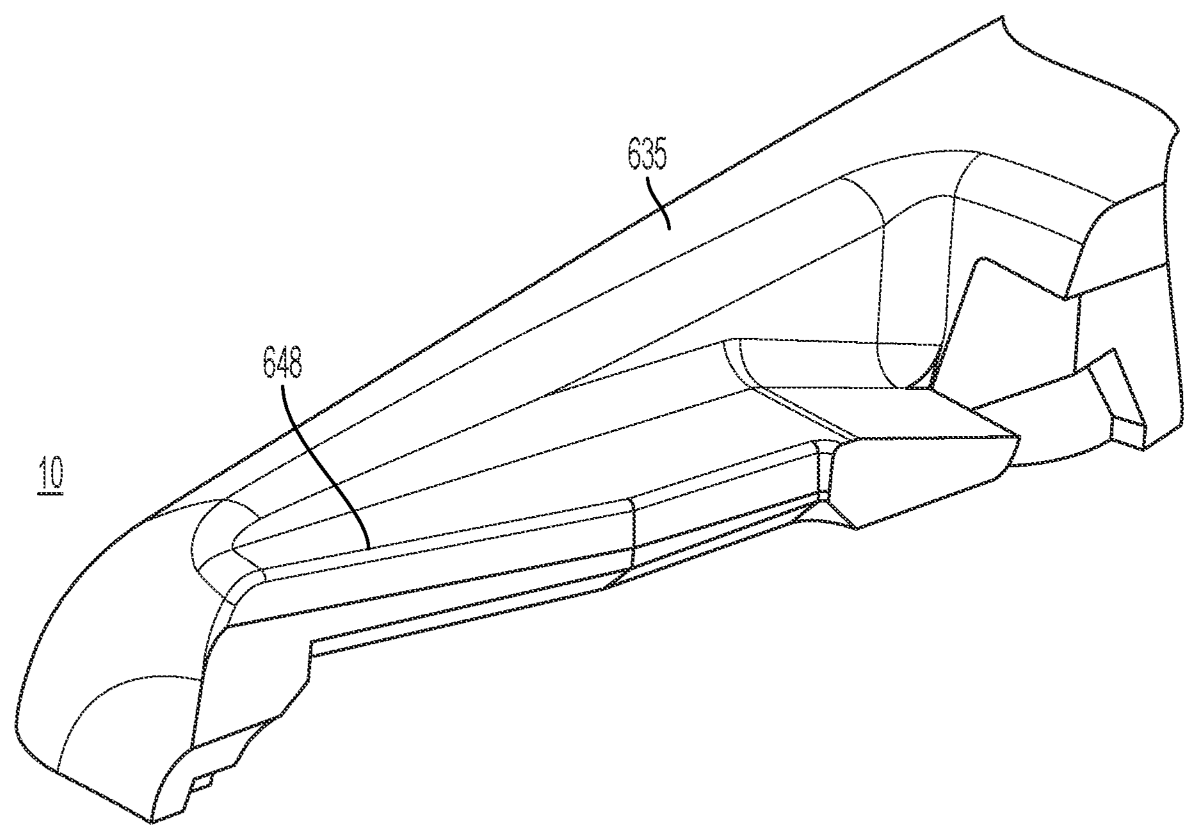

FIG. 15 illustrates the proximal end 10 of the handle 635 and the string control surface 648 which has a radiused edge instead of a sharp edge. Use of a radiused edge helps prevent the strings from being damaged or cut by the device during the insertion process.

Figure 16:
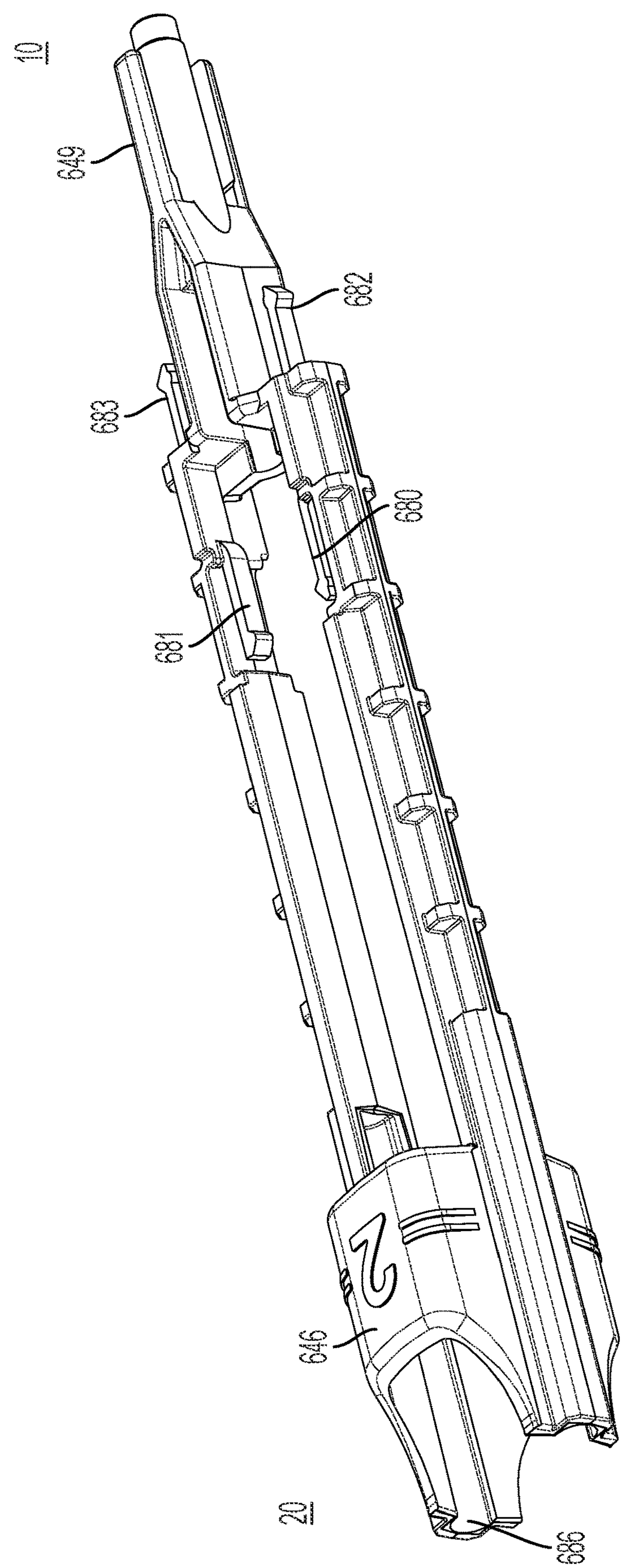

FIG. 16 illustrates the string control slider 646 which is a single molded part. The string control slider 646 has a proximal end 10 and a distal end 20. An interiorly facing channel 686 is formed along a portion of the length at the distal end in which the lateral rails of the sheath slider moves. The string control slider 646 has two pairs of detents. A first pair of interiorly engaging string control slider detent arms 680, 681 is positioned proximally relative to a pair of outwardly facing string control slider detent arms 682, 683. A pair of flexible arms 649 are positioned about the proximal end 10 of the string control slider 646 and positioned in a plane that is perpendicular to the plane in which the interiorly engaging string control slider detent arms 680, 681 and outwardly facing string control slider detent arms 682, 683 are positioned.

Figure 17B:
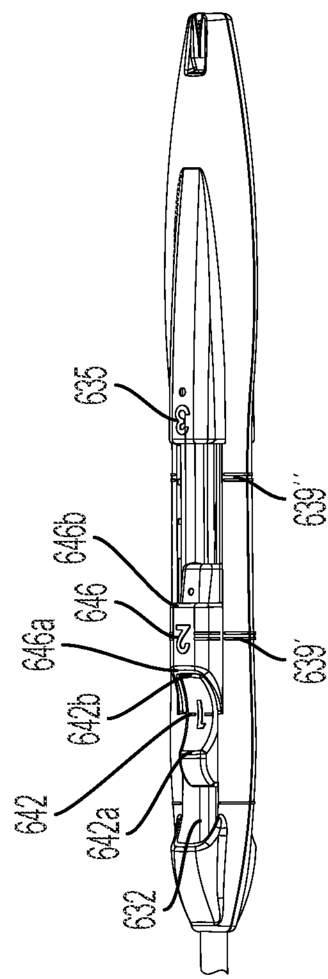
Figure 17B:
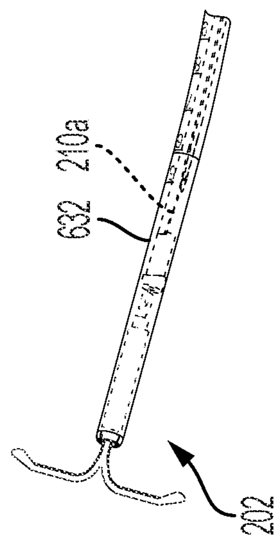

FIGS. 17A-C illustrate the proximal and distal end of the insertion device at phase 1 of the insertion process (FIG. 17A), phase 2 of the insertion process (FIG. 17B) and phase 3 of the insertion process (FIG. 17C). At each phase of the process, tactile feedback can be provided to the user when the interior components described and shown above are engaged.

In FIG. 17A, during phase 1, the t-shaped IUD 202 is loaded into the elongated sheath by pulling on the IUD strings 210 and is shown positioned within the interior of the elongated sheath 632 when the sheath slider 642 is positioned at a distal most position within the elongated channel in the handle 635. The distal surface of the sheath slider 642 aligns with the edge of the first cavity 645*a*. Additionally, the style of the marking 639 on the exterior surface of the handle 635 can align with a marking on the surface of the sheath slider 642 (shown as a single raised rib).

During phase 2, shown in FIG. 17B, the sheath slider 642 is moved proximally (towards the user) and slides under a portion of the string control slider 646 at which point, the plunger positioned within the elongated sheath 632 pushes the t-shaped IUD partially out of the distal end of the elongated sheath 632. The user will feel a click when the distally positioned sheath slider detent arms 672, 673 shown in FIG. 6D move past the lateral ribs 674, 675.—The IUD arms extend laterally away from a central axis, while the elongated body remains within the interior of the elongated sheath 632. During this phase the marking 639 on the handle 635 can align with markings on the string control slider 646 (shown as two adjacent raised ribs). When the sheath slider 642 is positioned optimally with respect to the string control slider 646, the proximal surface of the sheath slider 642 aligns with a surface of the string control slider 646*a*. Additionally, the interiorly engaging string control slider detent arms 680, 681 engage a pair of ribs 684, 685 which engage the plunger 634 on one side and the interiorly engage string control slider detent arms 680, 681 on the other side.

As shown in FIG. 17C, during phase 3, the sheath slider 642 and string control slider 646 are drawn further back in the channel at which point the entire t-shaped IUD is released from the distal end of the elongated sheath 632. The user will feel a click when the sheath slider 642 and string control slider 646 are moved together and an additional click when reaching the full proximal position. The sheath slider 642 and string control slider 646 are in the full proximal position along the longitudinal axis of the elongated channel 638, and at least partially surrounded by the second cavity 645B.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An insertion device for inserting an IUD comprising: an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; and a proximally positioned user interface, wherein the proximally positioned user interface further comprises an elongated channel on an upper user interface surface, a moveable sheath slider with an upper surface, a lower surface, two side surfaces, and a depression on the upper surface of the moveable sheath slider facing an exterior of the user interface, a lateral rail extending away from a first side surface of the two side surfaces, and a lateral detent arm extending away from a first side surface of the two side surfaces of the moveable sheath slider, and a string control slider having an interiorly facing slider channel and an interiorly facing detent in the interiorly facing slider channel, wherein the lateral rail of the moveable sheath slider slidably engages the interiorly facing slider channel of the string control slider and the moveable sheath slider is moveable within the elongated channel of the user interface and within the interiorly facing slider channel of the string control slider.

2. An insertion device for inserting an IUD comprising: an elongated sheath having a proximal end and a distal end, a lumen extending between the proximal end and the distal end wherein the elongated sheath defines an axis for operation of the insertion device and wherein the IUD is positionable within the elongated sheath; an elongated inner member having a proximal end and a distal end disposable within the lumen of the elongated sheath wherein a proximal end of the IUD is positionable adjacent the distal end of the elongated inner member; a proximally positioned user interface, wherein the proximally positioned user interface further comprises an elongated channel, a moveable sheath slider with an upper surface, a lower surface, two side surfaces, and a depression on as the upper surface of the moveable sheath slider facing an exterior of the user interface, an exterior rail extending away from a first side surface of the two side surfaces of the moveable sheath slider, and a lateral detent arm extending away from a first side surface of the two side surfaces of the moveable sheath slider, and a string control slider having a distal interior facing slider channel operable to receive the exterior rail of the moveable sheath sliders wherein the exterior rail of the moveable sheath slider slidably engages the interiorly facing slider channel of the string control slider and the moveable sheath slider is moveable within the elongated channel of the user interface and within the interiorly facing slider channel of the string control slider.

3. The insertion device of claim 2, wherein the proximally positioned user interface and the sheath slider further comprises one or more alignment surfaces, wherein the one or more alignment surfaces of the user interface is adapted and configured to mechanically complement one or more alignment surfaces of the sheath slider.

4. The insertion device of claim 2, wherein a first sheath slider alignment surface aligns with a first user interface alignment surface at a first position along a length of the elongated channel.

5. The insertion device of claim 2, wherein the string control slider is adaptable and configurable to securely move within the elongated channel.

6. The insertion device of claim 2, wherein the moveable sheath slider and the string control slider are adapted and configured to operate at least one of simultaneously and independently within the elongated channel.

7. The insertion device of claim 2, wherein the string control slider partially surrounds and the sheath slider.

8. The insertion device of claim 2, wherein the insertion device is configurable to receive the IUD within a distal end of the lumen of the elongated sheath and wherein the insertion device further comprises at least one string locking feature adaptable and configurable to secure one or more string components of the IUD.

9. The insertion device of claim 2, wherein the distal end of the elongated sheath has an atraumatic tip selected from the group comprising a rounded tip and a tapered tip.

10. The insertion device of claim 4, wherein the moveable sheath slider further comprises a second rail along a second side surface of the two side surfaces of the moveable sheath slider and a second lateral detent arm.

11. The insertion device of claim 2, wherein the moveable sheath slider further comprises a top half and a bottom half.

12. The insertion device of claim 2, wherein the string control slider further comprises an interiorly positioned hard stop.

13. The insertion device of claim 2, the user interface further comprises one or more string control slider detent arm in an interior of the user interface and a rib.

14. The insertion device of claim 13, wherein the one or more string control slider detent arms flex inwardly or flex outwardly.

15. The insertion device of claim 1, wherein a first sheath slider alignment surface aligns with a first user interface alignment surface at a first position along a length of the elongated channel.

16. The insertion device of claim 1, wherein the string control slider is adaptable and configurable to securely move within the elongated channel.

17. The insertion device of claim 1, wherein the moveable sheath slider and the string control slider are adapted and configured to operate at least one of simultaneously and independently within the elongated channel.

18. The insertion device of claim 1, wherein the string control slider partially surrounds and the sheath slider.

19. The insertion device of claim 1, wherein the insertion device is configurable to receive the IUD within a distal end of the lumen of the elongated sheath and wherein the insertion device further comprises at least one string locking feature adaptable and configurable to secure one or more string components of the IUD.

20. The insertion device of claim 1, wherein the distal end of the elongated sheath has an atraumatic tip selected from the group comprising a rounded tip and a tapered tip.

21. The insertion device of claim 1, wherein the moveable sheath slider further comprises a second lateral rail along a second side surface of the two side surfaces of the moveable sheath slider and a second lateral detent arm.

22. The insertion device of claim 1, wherein the moveable sheath slider further comprises a top half and a bottom half.

23. The insertion device of claim 1, wherein the string control slider further comprises an interiorly positioned hard stop.

24. The insertion device of claim 1, the user interface further comprises one or more string control slider detent arm in an interior of the user interface and a rib.

25. The insertion device of claim 1, wherein the one or more lateral detent arms flex inwardly or flex outwardly.

26. The insertion device of claim 1 wherein an elongate member of the IUD comprises a core part around which a jacket-like polymeric reservoir containing an active agent has been fitted.

27. The insertion device of claim 26 wherein the active agent is a hormone used for the treatment of menopausal troubles or for contraception.

28. The insertion device of claim 27 wherein the hormone is levonorgestrel.

29. The insertion device of claim 1 wherein the IUD includes an active agent that is a hormone used for treatment of menopausal troubles or for contraception.

30. The insertion device of claim 29 wherein the hormone is levonorgestrel.

31. The insertion device of claim 2 wherein an elongate member of the IUD comprises a core part around which a jacket-like polymeric reservoir containing an active agent has been fitted.

32. The insertion device of claim 31 wherein the active agent is a hormone used for the treatment of menopausal troubles or for contraception.

33. The insertion device of claim 32 wherein the hormone is levonorgestrel.

34. The insertion device of claim 2 wherein the IUD includes an active agent that is a hormone used for treatment of menopausal troubles or for contraception.

35. The insertion device of claim 34 wherein the hormone is levonorgestrel.

* * * * *